United States Patent
Storkan et al.

(10) Patent No.: US 6,923,937 B2
(45) Date of Patent: *Aug. 2, 2005

(54) EMULSIFIED SOIL BIOCIDES USED IN DRIP IRRIGATION SYSTEMS

(75) Inventors: Dean C. Storkan, Pebble Beach, CA (US); Mark A. McCaslin, Temecula, CA (US); Matthew J. Gillis, Hollister, CA (US)

(73) Assignee: Trical, Inc., Hollister, CA (US)

( * ) Notice: Subject to any disclaimer, the term of this patent is extended or adjusted under 35 U.S.C. 154(b) by 56 days.

This patent is subject to a terminal disclaimer.

(21) Appl. No.: 10/351,072

(22) Filed: Jan. 24, 2003

(65) Prior Publication Data

US 2003/0219355 A1 Nov. 27, 2003

Related U.S. Application Data

(63) Continuation-in-part of application No. 09/736,629, filed on Dec. 13, 2000.

(51) Int. Cl.⁷ .................................................. A61L 9/00
(52) U.S. Cl. ........................ 422/32; 47/DIG. 10; 422/1; 422/28; 422/37
(58) Field of Search ................................ 422/1, 28, 32, 422/37, 40; 47/DIG. 9, DIG. 10; 504/116, 100, 107; 514/429

(56) References Cited

U.S. PATENT DOCUMENTS

| | | | | |
|---|---|---|---|---|
| 4,828,835 A | * | 5/1989 | Meyers et al. | 424/409 |
| 5,340,593 A | * | 8/1994 | Green et al. | 424/715 |
| 5,656,571 A | * | 8/1997 | Miller et al. | 504/361 |
| 5,674,514 A | * | 10/1997 | Hasslin | 424/405 |
| 5,846,904 A | * | 12/1998 | Imai et al. | 504/361 |

* cited by examiner

Primary Examiner—Krisanne Jastrzab
(74) Attorney, Agent, or Firm—Burns, Doane, Swecker & Mathis LLP

(57) ABSTRACT

A soil biocide formulation for aqueous delivery comprising from about 50 to 99% by weight of the formulation of a fumigant preferably selected from the group consisting of methyl bromide, chloropicrin, 1-3 dichloropropene (Telone), propargyl bromide, dimethyl disulphide methylisothiocyanate and mixtures of them; and from about 50 to 1% emulsifier with the emulsifier being comprised of non-ionic and anionic surfactants.

6 Claims, 20 Drawing Sheets

Treatment of Different Types of Tubing with Chloropicrin Formulation

| Tubing Type | Immediate Rx | Wall Thickness After 15 Hours | Elasticity/Strength After 15 Hours | General Appearance Integrity After 15 Hours |
|---|---|---|---|---|
| Black Seamless Latex | None | No change | Maintained | No effect |
| FEP Teflon | None | No change | Maintained | No effect |
| Nalgene 860 Tissue Culture Grade | None | No change | Maintained | Sticky |
| Manosil | None | No change | Maintained | No effect |
| Tygon R3603 | None | Reduced thickness | Reduced slightly | Appeared melted |
| Nalgene 180 Premium PVC | None | Reduced thickness | Reduced slightly | Slightly opaque, appeared melted |

FIG. 3

Nematode Efficacy - Chloropicrin       Drip Application
of Various EC Percentages
Summary of Results

| Cylinder # | Nematode Species [a] | | | | | | | |
|---|---|---|---|---|---|---|---|---|
| | Root Knot (Meloidogyne) | Dagger (Xiphinema) | Citrus | Pin | Root Knot (Meloidogyne) [yue] | Dagger (Xiphinema) | Citrus | Pin |
| | — Counts — | | | | — Adjusted Counts — [§] | | | |
| 1 | 5 | 3 | 168 | 0 | 15 | 9 | 504 | 0 |
| 2 | 22 | 4 | 216 | 28 | 66 | 12 | 648 | 84 |
| 3 | 1 | 2 | 456 | 0 | 3 | 6 | 1368 | 0 |
| 4 | 49 | 0 | 338 | 9 | 147 | 0 | 1014 | 27 |
| 5 | 0 | 0 | 7 | 4 | 0 | 0 | 21 | 0 |
| 6 | 23 | 0 | 40 | 14 | 69 | 0 | 120 | 42 |
| 7 | 112 | 0 | 80 | 0 | 336 | 0 | 240 | 0 |
| 8 | 29 | 0 | 79 | 0 | 87 | 0 | 237 | 0 |
| 9 | 0 | 0 | 114 | 0 | 0 | 0 | 342 | 0 |
| 10 | 16 | 0 | 72 | 0 | 48 | 0 | 216 | 0 |
| 11 | 22 | 0 | 160 | 0 | 66 | 0 | 480 | 0 |
| 12 | 29 | 0 | 87 | 0 | 87 | 0 | 261 | 0 |
| 13 | 115 | 0 | 136 | 0 | 345 | 0 | 408 | 0 |
| 14 | 16 | 0 | 30 | 0 | 48 | 0 | 90 | 0 |
| 15 | 22 | 0 | 31 | 0 | 66 | 0 | 93 | 0 |
| 16 | 79 | 0 | 82 | 0 | 237 | 0 | 246 | 0 |
| 17 | 15 | 0 | 17 | 0 | 45 | 0 | 51 | 0 |
| 18 | 30 | 0 | 81 | 0 | 90 | 0 | 243 | 0 |
| 19 | 69 | 0 | 109 | 0 | 207 | 0 | 327 | 0 |
| 20 | 26 | 0 | 68 | 0 | 78 | 0 | 204 | 0 |

§ 33% extraction efficiency, measured values multiplied by 3
[a] *No counts were obtained for Ring nematode statistical analysis.*

FIG. 4

Chloropicrin EC - Lab Tests for Weed Seed Mortality
PIGWEED
Weed Seed: *Amaranthus retroflexus*

Treatment Date = 10/28/1999  Number of Seeds/Dish = 100

| | Treatment | Seed Germination Counts | | | | | | | | | (% Mortality) | | | | | | | | | | |
|---|---|---|---|---|---|---|---|---|---|---|---|---|---|---|---|---|---|---|---|---|---|
| | | Date of Count = 11/05/1999 | | | | Date of Count = 11/09/1999 | | | | Date of Count = 11/05/1999 | | | | | Date of Count = 11/09/1999 | | | | | | |
| | | Elapsed Time from Treatment = 8 Days | | | | Elapsed Time from Treatment = 12 Days | | | | Elapsed Time from Treatment = 8 Days | | | | | Elapsed Time from Treatment = 12 Days | | | | | | |
| | | 1st Count | | | | 2nd Count | | | | 1st Count | | | | | 2nd Count | | | | | 2nd Count at 12 Days | % Mortality |
| Seed Age | Treatment Solution | Rep 1 | Rep 2 | Rep 3 | Rep 4 | Rep 1 | Rep 2 | Rep 3 | Rep 4 | Rep 1 | Rep 2 | Rep 3 | Rep 4 | Mean | Rep 1 | Rep 2 | Rep 3 | Rep 4 | Mean | | Above Control |
| NEW SEED | Control 0 ppm, 0% Emulsifier | 26 | 29 | 15 | 20 | 75 | 65 | 55 | 75 | 74% | 71% | 85% | 80% | 78% | 25% | 34% | 45% | 25% | 32% | | 0% |
| NEW SEED | 0 ppm, 5% Emulsifier | 13 | 9 | 10 | 14 | 15 | 16 | 21 | 32 | 87% | 91% | 90% | 86% | 89% | 85% | 84% | 79% | 68% | 79% | | 47% |
| NEW SEED | 0 ppm, 50% Emulsifier | 6 | 2 | 12 | 4 | 10 | 4 | 19 | 6 | 94% | 98% | 88% | 96% | 94% | 90% | 96% | 81% | 94% | 90% | | 58% |
| NEW SEED | 500 ppm, 5% Emulsifier | 0 | 3 | 1 | 4 | 0 | 3 | 1 | 4 | 100% | 97% | 99% | 96% | 98% | 100% | 97% | 99% | 96% | 98% | | 66% |
| NEW SEED | 500 ppm, 50% Emulsifier | 0 | 2 | 0 | 2 | 3 | 6 | 3 | 7 | 7% | 98% | 100% | 98% | 76% | 97% | 94% | 97% | 93% | 95% | | 63% |
| NEW SEED | 1000 ppm, 5% Emulsifier | 4 | 1 | 1 | 1 | 4 | 2 | 3 | 1 | 96% | 99% | 99% | 100% | 99% | 91% | 98% | 99% | 99% | 97% | | 65% |
| NEW SEED | 1000 ppm, 50% Emulsifier | 0 | 0 | 0 | 0 | 0 | 0 | 0 | 0 | 100% | 100% | 100% | 100% | 100% | 100% | 100% | 100% | 100% | 100% | | 68% |
| OLD SEED | Control 0 ppm, 0% Emulsifier | | | | | | | | | | | | | | | | | | | | |
| OLD SEED | 0 ppm, 5% Emulsifier | | | | | | | | | | | | | | | | | | | | |
| OLD SEED | 0 ppm, 50% Emulsifier | | | | | | | | | | | | | | | | | | | | |
| OLD SEED | 500 ppm, 5% Emulsifier | | | | | | | | | | | | | | | | | | | | |
| OLD SEED | 500 ppm, 50% Emulsifier | | | | | | | | | | | | | | | | | | | | |
| OLD SEED | 1000 ppm, 5% Emulsifier | | | | | | | | | | | | | | | | | | | | |
| OLD SEED | 1000 ppm, 50% Emulsifier | | | | | | | | | | | | | | | | | | | | |

HIGHLY SIGNIFICANT DIFFERENCE @ 99%

NEW SEED
Anova: Single Factor

SUMMARY

| Groups | Count | Sum | Average | Variance |
|---|---|---|---|---|
| Row 1 | 4 | 1.28 | 0.3225 | 0.008025 |
| Row 2 | 4 | 3.16 | 0.79 | 0.00606667 |
| Row 3 | 4 | 3.61 | 0.9025 | 0.004425 |
| Row 4 | 4 | 3.92 | 0.98 | 0.00033333 |
| Row 5 | 4 | 3.81 | 0.9525 | 0.000425 |
| Row 6 | 4 | 3.87 | 0.9675 | 0.00149167 |
| Row 7 | 4 | 4 | 1 | 0 |

ANOVA

| Source of Variation | SS | df | MS | F | P-value | F crit |
|---|---|---|---|---|---|---|
| Between Groups | 1.3826 | 6 | 0.2321 | 74.5416539 | 4.547E-13 | 5.8867927 |
| Within Groups | 0.0653 | 21 | 0.0031095 | | | |
| Total | 1.4579 | 27 | | | | |

FIG. 5a

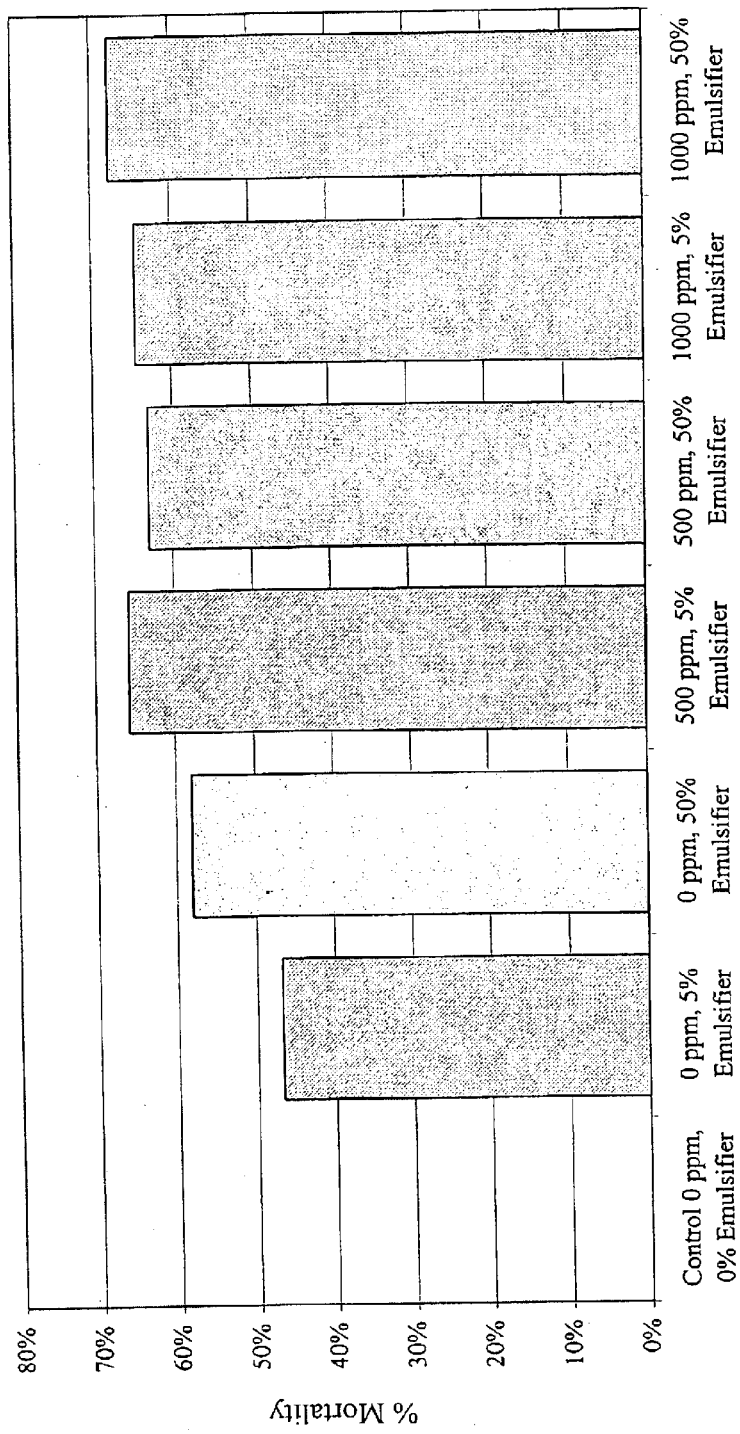

FIG. 6a

Chloropicrin EC - Lab Tests for Weed Seed Mortality
WILD MUSTARD
Weed Seed: *Brassica kaber*

Treatment Date = 10/28/1999    Number of Seeds/Dish = 100

Seed Germination Counts

| Seed Age | Treatment | Treatment Schism | 1st Count Rep1 | Rep2 | Rep3 | Rep4 | 2nd Count Rep1 | Rep2 | Rep3 | Rep4 | 1st Count at 8 Days Mean | 2nd Count (% Mortality) 1st Count Rep1 | Rep2 | Rep3 | Rep4 | Mean | 2nd Count Rep1 | Rep2 | Rep3 | Rep4 | 2nd Count at 12 Days Mean | % Mortality Above Control |
|---|---|---|---|---|---|---|---|---|---|---|---|---|---|---|---|---|---|---|---|---|---|---|

Date of Count = 11/05/1999, Elapsed Time from Treatment = 8 Days
Date of Count = 11/09/1999, Elapsed Time from Treatment = 12 Days

| Seed Age | Treatment | Rep1 | Rep2 | Rep3 | Rep4 | Rep1 | Rep2 | Rep3 | Rep4 | Rep1 | Rep2 | Rep3 | Rep4 | Mean | Rep1 | Rep2 | Rep3 | Rep4 | Mean | %MAC |
|---|---|---|---|---|---|---|---|---|---|---|---|---|---|---|---|---|---|---|---|---|
| NEW SEED | Control 0 ppm, 0% Emulsifier | 35 | 38 | 40 | 33 | 60 | 51 | 49 | 54 | 65% | 62% | 60% | 67% | 64% | 40% | 49% | 51% | 46% | 47% | 0% |
| NEW SEED | 0 ppm, 5% Emulsifier | 34 | 29 | 32 | 28 | 80 | 78 | 75 | 79 | 66% | 71% | 68% | 72% | 69% | 20% | 22% | 25% | 21% | 22% | -25% |
| NEW SEED | 0 ppm, 50% Emulsifier | 28 | 31 | 29 | 32 | 81 | 77 | 70 | 82 | 72% | 69% | 71% | 68% | 70% | 19% | 23% | 30% | 18% | 23% | -24% |
| NEW SEED | 500 ppm, 5% Emulsifier | 34 | 16 | 35 | 36 | 82 | 72 | 91 | 88 | 66% | 84% | 65% | 64% | 70% | 18% | 28% | 9% | 12% | 17% | -30% |
| NEW SEED | 500 ppm, 50% Emulsifier | 40 | 26 | 10 | 24 | 83 | 76 | 80 | 85 | 60% | 74% | 90% | 76% | 75% | 17% | 24% | 20% | 15% | 19% | -28% |
| NEW SEED | 1000 ppm, 5% Emulsifier | 30 | 31 | 18 | 22 | 81 | 80 | 70 | 76 | 70% | 69% | 82% | 78% | 75% | 19% | 20% | 30% | 24% | 23% | -23% |
| NEW SEED | 1000 ppm, 50% Emulsifier | 31 | 11 | 3 | 41 | 36 | 13 | 12 | 41 | 69% | 89% | 97% | 59% | 79% | 64% | 87% | 88% | 59% | 75% | 28% |

Date of Count = 11/08/1999, Elapsed Time from Treatment = 11 Days

| OLD SEED | Control 0 ppm, 0% Emulsifier | 0 | 1 | 0 | 1 | 0 | 1 | 0 | 1 | 100% | 99% | 100% | 99% | 100% | 100% | 99% | 100% | 99% | 100% | 0% |
| OLD SEED | 0 ppm, 5% Emulsifier | 2 | 2 | 0 | 1 | 2 | 2 | 0 | 1 | 98% | 98% | 100% | 99% | 99% | 98% | 98% | 100% | 99% | 99% | -1% |
| OLD SEED | 0 ppm, 50% Emulsifier | 1 | 0 | 0 | 0 | 1 | 0 | 0 | 0 | 99% | 100% | 100% | 100% | 100% | 99% | 100% | 100% | 99% | 100% | 0% |
| OLD SEED | 500 ppm, 5% Emulsifier | 2 | 0 | 0 | 0 | 2 | 0 | 0 | 0 | 98% | 100% | 100% | 100% | 100% | 98% | 100% | 100% | 100% | 100% | 0% |
| OLD SEED | 500 ppm, 50% Emulsifier | 3 | 2 | 3 | 0 | 3 | 2 | 3 | 0 | 97% | 98% | 97% | 100% | 98% | 97% | 98% | 97% | 100% | 98% | -2% |
| OLD SEED | 1000 ppm, 5% Emulsifier | 0 | 0 | 0 | 0 | 0 | 0 | 0 | 0 | 100% | 100% | 100% | 100% | 100% | 100% | 100% | 100% | 100% | 100% | 0% |
| OLD SEED | 1000 ppm, 50% Emulsifier | 0 | 0 | 0 | 0 | 0 | 0 | 0 | 0 | 100% | 100% | 100% | 100% | 100% | 100% | 100% | 100% | 100% | 100% | 0% |

NEW SEED
Anova: Single Factor

SUMMARY

| Groups | Count | Sum | Average | Variance |
|---|---|---|---|---|
| Row 1 | 4 | 1.86 | 0.465 | 0.0023 |
| Row 2 | 4 | 0.88 | 0.22 | 0.000466667 |
| Row 3 | 4 | 0.9 | 0.225 | 0.002966667 |
| Row 4 | 4 | 0.67 | 0.1675 | 0.007025 |
| Row 5 | 4 | 0.76 | 0.19 | 0.001833333 |
| Row 6 | 4 | 0.93 | 0.2325 | 0.002491657 |
| Row 7 | 4 | 2.98 | 0.745 | 0.022966667 |

ANOVA

| Source of Variation | SS | df | MS | F | P-value | F crit |
|---|---|---|---|---|---|---|
| Between Groups | 1.0739357 | 6 | 0.17895863 | 31.52012579 | 1.866E-09 | 3.8117491 |
| Within Groups | 0.119925 | 21 | 0.0056786 | | | |
| Total | 1.1931857 | 27 | | | | |

SIGNIFICANT DIFFERENCE @ 99%

OLD SEED
Anova: Single Factor

SUMMARY

| Groups | Count | Sum | Average | Variance |
|---|---|---|---|---|
| Row 1 | 4 | 3.98 | 0.995 | 3.33333E-05 |
| Row 2 | 4 | 3.95 | 0.9875 | 9.1666 7E-05 |
| Row 3 | 4 | 3.98 | 0.995 | 3.33333E-05 |
| Row 4 | 4 | 3.98 | 0.995 | 1E-04 |
| Row 5 | 4 | 3.92 | 0.98 | 0.0002 |
| Row 6 | 4 | 4 | 1 | 0 |
| Row 7 | 4 | 4 | 1 | 0 |

ANOVA

| Source of Variation | SS | df | MS | F | P-value | F crit |
|---|---|---|---|---|---|---|
| Between Groups | 0.001236 | 6 | 0.000206 | 3.145454545 | 0.023236 | 2.572742 |
| Within Groups | 0.001375 | 21 | 6.55E-05 | | | |
| Total | 0.002611 | 27 | | | | |

SIGNIFICANT DIFFERENCE @ 95%

FIG. 7a

Chloropicrin EC - Lab Tests for Weed Seed Mortality
YELLOW
NUTGRASS
Weed Seed: *Cyperus esculintus*    Treatment Date = 10/28/1999    Number of Seeds/Dish = 100

| | Treatment | Seed Germination Counts | | | | | | | | | (% Mortality) | | | | | | | | | | | |
|---|---|---|---|---|---|---|---|---|---|---|---|---|---|---|---|---|---|---|---|---|---|---|
| | | Date of Count = 11/05/1999 | | | | Date of Count = 11/09/1999 | | | | | 1st Count | | | | 1st Count at 8 Days | 2nd Count | | | | 2nd Count at 12 Days | % Mortality Above Control |
| | | Elapsed Time from Treatment = 8 Days | | | | Elapsed Time from Treatment = 12 Days | | | | | | | | | | | | | | | |
| Seed Age | Treatment Solution | Rep 1 | Rep 2 | Rep 3 | Rep 4 | Rep 1 | Rep 2 | Rep 3 | Rep 4 | Rep 1 | Rep 2 | Rep 3 | Rep 4 | Mean | Rep 1 | Rep 2 | Rep 3 | Rep 4 | Mean | |
| NEW SEED | Control 0 ppm, 0% Emulsifier | 0 | 0 | 0 | 0 | 0 | 0 | 0 | 0 | 100% | 100% | 100% | 100% | 100% | 100% | 100% | 100% | 100% | 100% | 0% |
| NEW SEED | 0 ppm, 5% Emulsifier | 0 | 0 | 0 | 0 | 0 | 0 | 0 | 0 | 100% | 100% | 100% | 100% | 100% | 100% | 100% | 100% | 100% | 100% | 0% |
| NEW SEED | 0 ppm, 50% Emulsifier | 0 | 0 | 0 | 0 | 0 | 0 | 0 | 0 | 100% | 100% | 100% | 100% | 100% | 100% | 100% | 100% | 100% | 100% | 0% |
| NEW SEED | 500 ppm, 5% Emulsifier | 0 | 0 | 0 | 0 | 0 | 0 | 0 | 5 | 100% | 100% | 100% | 100% | 100% | 100% | 100% | 100% | 95% | 99% | -1% |
| NEW SEED | 500 ppm, 50% Emulsifier | 0 | 0 | 0 | 0 | 0 | 2 | 0 | 2 | 99% | 100% | 100% | 100% | 100% | 99% | 98% | 100% | 98% | 100% | -1% |
| NEW SEED | 1000 ppm, 5% Emulsifier | 0 | 0 | 0 | 0 | 1 | 2 | 0 | 0 | 100% | 100% | 100% | 100% | 100% | 99% | 98% | 100% | 100% | 99% | -1% |
| NEW SEED | 1000 ppm, 50% Emulsifier | 0 | 0 | 0 | 0 | 0 | 0 | 0 | 0 | 100% | 100% | 100% | 100% | 100% | 100% | 100% | 100% | 100% | 100% | 0% |
| | | Date of Count = 11/08/1999 | | | | | | | | | | | | | | | | | | | |
| | | Elapsed Time from Treatment = 11 Days | | | | | | | | | | | | | | | | | | | |
| OLD SEED | Control 0 ppm, 0% Emulsifier | 0 | 0 | 0 | 0 | | | | | 100% | 100% | 100% | 100% | 100% | 100% | 100% | 100% | 100% | 100% | 0% |
| OLD SEED | 0 ppm, 5% Emulsifier | 0 | 0 | 0 | 0 | | | | | 100% | 100% | 100% | 100% | 100% | 100% | 100% | 100% | 100% | 100% | 0% |
| OLD SEED | 0 ppm, 50% Emulsifier | 0 | 0 | 0 | 0 | | | | | 100% | 100% | 100% | 100% | 100% | 100% | 100% | 100% | 100% | 100% | 0% |
| OLD SEED | 500 ppm, 5% Emulsifier | 0 | 0 | 0 | 0 | | | | | 100% | 100% | 100% | 100% | 100% | 100% | 100% | 100% | 100% | 100% | 0% |
| OLD SEED | 500 ppm, 50% Emulsifier | 0 | 0 | 0 | 0 | | | | | 100% | 100% | 100% | 100% | 100% | 100% | 100% | 100% | 100% | 100% | 0% |
| OLD SEED | 1000 ppm, 5% Emulsifier | 0 | 0 | 0 | 0 | | | | | 100% | 100% | 100% | 100% | 100% | 100% | 100% | 100% | 100% | 100% | 0% |
| OLD SEED | 1000 ppm, 50% Emulsifier | 0 | 0 | 0 | 0 | | | | | 100% | 100% | 100% | 100% | 100% | 100% | 100% | 100% | 100% | 100% | 0% |

NEW SEED    No Significance         OLD SEED    No Significance
Anova: Single Factor

SUMMARY

| Groups | Count | Sum | Average | Variance |
|---|---|---|---|---|
| Row 1 | 4 | | 1 | 0 |
| Row 2 | 4 | | 1 | 0 |
| Row 3 | 4 | | 1 | 0 |
| Row 4 | 4 | 3.95 | 0.9875 | 0.000625 |
| Row 5 | 4 | 3.98 | 0.995 | 1E-04 |
| Row 6 | 4 | 3.97 | 0.9925 | 9.1667E-05 |
| Row 7 | 4 | | 1 | 0 |

ANOVA

| Source of Variation | SS | df | MS | F | P-value | F crit |
|---|---|---|---|---|---|---|
| Between Groups | 0.0008929 | 6 | 9.881E-05 | 0.84093076 | 0.5494524 | 2.5727118 |
| Within Groups | 0.00245 | 21 | 0.00011167 | | | |
| Total | 0.0030429 | 27 | | | | |

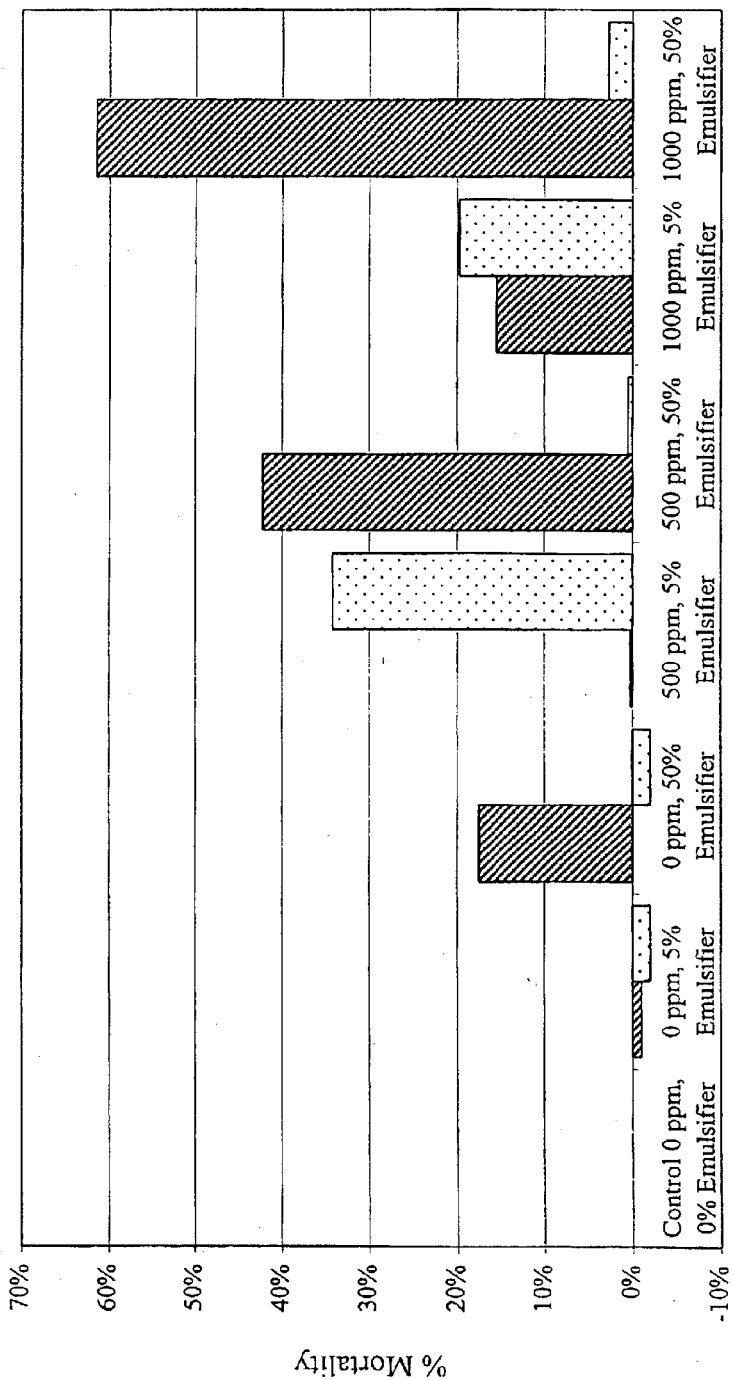
FIG: 10b

Chloropicrin EC - Lab Tests for Weed Seed Mortality
BINDWEED
Weed Seed: *Convolvulus arvensis*    Treatment Date = 10/28/1999    Number of Seeds/Dish = 100

| Treatment | | Seed Germination Counts | | | | | | | | (% Mortality) | | | | | | | | | | |
|---|---|---|---|---|---|---|---|---|---|---|---|---|---|---|---|---|---|---|---|---|
| | | 1st Count | | | | 2nd Count | | | | 1st Count | | | | 1st Count at 8 Days | 2nd Count | | | | 2nd Count at 12 Days | % Mortality Above Control |
| | | Date of Count = 11/05/1999 | | | | Date of Count = 11/09/1999 | | | | | | | | | | | | | | |
| | | Elapsed Time from Treatment = 8 Days | | | | Elapsed Time from Treatment = 12 Days | | | | | | | | | | | | | | |
| Seed Age | Treatment Solution | Rep 1 | Rep 2 | Rep 3 | Rep 4 | Rep 1 | Rep 2 | Rep 3 | Rep 4 | Rep 1 | Rep 2 | Rep 3 | Rep 4 | Mean | Rep 1 | Rep 2 | Rep 3 | Rep 4 | Mean | |
| NEW SEED | Control 0 ppm, 0% Emulsifier | 15 | 20 | 23 | 28 | 80 | 84 | 83 | 78 | 85% | 80% | 77% | 72% | 79% | 20% | 16% | 17% | 22% | 19% | 0% |
| NEW SEED | 0 ppm, 5% Emulsifier | 16 | 22 | 23 | 14 | 29 | 29 | 27 | 18 | 84% | 78% | 77% | 86% | 81% | 71% | 71% | 73% | 82% | 74% | 55% |
| NEW SEED | 0 ppm, 50% Emulsifier | 19 | 15 | 15 | 16 | 51 | 63 | 55 | 65 | 81% | 85% | 85% | 84% | 84% | 49% | 37% | 45% | 35% | 42% | 23% |
| NEW SEED | 500 ppm, 5% Emulsifier | 12 | 16 | 14 | 7 | 54 | 63 | 55 | 65 | 88% | 84% | 86% | 93% | 88% | 46% | 37% | 45% | 35% | 41% | 22% |
| NEW SEED | 500 ppm, 50% Emulsifier | 25 | 13 | 22 | 17 | 62 | 13 | 74 | 56 | 75% | 87% | 78% | 83% | 81% | 38% | 87% | 26% | 44% | 49% | 30% |
| NEW SEED | 1000 ppm, 5% Emulsifier | 8 | 15 | 5 | 12 | 14 | 20 | 10 | 16 | 92% | 85% | 95% | 88% | 90% | 86% | 80% | 90% | 84% | 85% | 66% |
| NEW SEED | 1000 ppm, 50% Emulsifier | 5 | 8 | 3 | 4 | 7 | 15 | 7 | 10 | 95% | 92% | 97% | 96% | 95% | 93% | 85% | 93% | 90% | 90% | 72% |
| OLD SEED | Control 0 ppm, 0% Emulsifier | | | | | | | | | | | | | | | | | | | |
| OLD SEED | 0 ppm, 5% Emulsifier | | | | | | | | | | | | | | | | | | | |
| OLD SEED | 0 ppm, 50% Emulsifier | | | | | | | | | | | | | | | | | | | |
| OLD SEED | 500 ppm, 5% Emulsifier | | | | | | | | | | | | | | | | | | | |
| OLD SEED | 500 ppm, 50% Emulsifier | | | | | | | | | | | | | | | | | | | |
| OLD SEED | 1000 ppm, 5% Emulsifier | | | | | | | | | | | | | | | | | | | |
| OLD SEED | 1000 ppm, 50% Emulsifier | | | | | | | | | | | | | | | | | | | |

SIGNIFICANT DIFFERENCE @ 99%

NEW SEED
Anova: Single Factor

SUMMARY

| Groups | Count | Sum | Average | Variance |
|---|---|---|---|---|
| Row 1 | 4 | 0.75 | 0.1875 | 0.00075833 |
| Row 2 | 4 | 2.97 | 0.7425 | 0.00275833 |
| Row 3 | 4 | 1.66 | 0.415 | 0.00435867 |
| Row 4 | 4 | 1.63 | 0.4075 | 0.00309167 |
| Row 5 | 4 | 1.96 | 0.4875 | 0.070625 |
| Row 6 | 4 | 3.4 | 0.85 | 0.00173333 |
| Row 7 | 4 | 3.61 | 0.9025 | 0.001425 |

ANOVA

| Source of Variation | SS | df | MS | F | P-value | F crit |
|---|---|---|---|---|---|---|
| Between Groups | 1.8890214 | 6 | 0.28150356 | 23.2487464 | 2.866E-08 | 3.8117491 |
| Within Groups | 0.254275 | 21 | 0.0121083 | | | |
| Total | 1.9432964 | 27 | | | | |

FIG. 11a

EMULSIFIED SOIL BIOCIDES USED IN DRIP IRRIGATION SYSTEMS

CROSS REFERENCE TO RELATED APPLICATION

This Application is a continuation in part (CIP) of and incorporates by reference U.S. application Ser. No. 09/736,629 filed Dec. 13, 2000, and titled "EMULSIFIED SOIL BIOCIDES USED IN DRIP IRRIGATION SYSTEMS".

FIELD OF THE INVENTION

The present invention relates generally to a soil biocide formulation that provides enhanced efficacy in controlling or suppressing nematodes such as root knot nematodes, dagger nematodes, citrus nematodes and pin nematodes, and weeds such as pigweed, white sweet clover, wild mustard, yellow nut grass, yellow sweet clover, barnyard grass and bindweed and more particularly to a soil fumigant formulation that can be applied through a drip irrigation system without causing any corrosive damage to the irrigation systems, and that also reduces exposure of farm workers to the harmful effects of soil biocides.

BACKGROUND OF THE INVENTION

The importance of the control of plant pathogens, nematodes and weeds cannot be underestimated in the agriculture industry. Therefore, a complete destruction of plant pathogens or at least a substantial reduction is an often-encountered challenge in the agriculture industry. Pathogenic organisms afflict root systems of various kinds of crops and severely inhibit their growth, causing severe damage to the plants. In order to circumvent these problems, different mechanisms are often adopted to control the harmful effects of pathogenic organisms on plants and to enhance the productivity and improve the viability of plants.

Traditional methods such as crop rotation or fallowing the fields for as long as four years and use of pathogen-resistant crops are among the most common methods for control of pathogenic organisms. Crop rotation though widely used, is not highly advantageous because of its limited utility in controlling the plethora of pathogens that afflict crops. Further, crop rotation results in diminished overall productivity owing to the low per acre return that is usually obtained from non-host crops. Use of pathogen-resistant varieties of crops has a vast potential. However, a severe lack of pathogen resistant varieties of many crops causes this mechanism to be limited in efficacy.

Soil fumigation is another tool used for the control of plant pathogens. Chief among the crops which benefit from soil fumigants are strawberries, grapes, peppers, onions, deciduous fruits and nuts, turf, cut flowers, and tree and seedling nurseries. Some of the most effective soil fumigants are methyl bromide, chloropicrin, 1-3 dichloropropene, dimethyl disulphide, propargyl bromide, and methylisothiocyanate, or their mixtures, which are selected in various ratios and strength, depending on the target soil pests and soil variances such as temperature, texture and moisture. Most soil fumigants are composed of organic chemicals that are distributed within the soil as gases to either inhibit or kill destructive organisms. Soil fumigants are chemical compounds in the form of sulphur containing compounds and halogenated compounds.

The soil fumigants owe their effectiveness as soil biocides to their gaseous nature that allows them to spread though soil easily and reasonably uniformly. For instance, a soil fumigant such as methyl bromide, a colorless gas at room temperature, is commonly compressed into liquid form for purposes of application. After application in liquid form, methyl bromide penetrates the soil rapidly through air spaces between soil particles and then kills or suppresses pathogenic organisms. Other soil fumigants such as chloropicrin are also commonly employed for the control of bacteria, fungi, and insects because they also display similar soil penetration capabilities.

Traditionally, a field is prepared prior to fumigation by tilling and irrigating the soil so as to ensure proper soil texture and moisture content of the soil. Typically following preparation is a process called pre-plant soil fumigation, in which a commercial fumigator enters the field with a tractor with a rear mounted tool bar, to which is attached plumbed shanks that penetrate the soil and deliver the pre-plant soil fumigant to the desired depth. If desired, the field then may be tarped with a polyethylene film, which is applied by a roller attached to the tractor. Normally, the field is ready for planting thereafter within two weeks.

However, soil fumigants suffer from several drawbacks. First, though effective in lighter, sandier soils, soil fumigants are not as effective in heavier soils. When used in lighter, sandier soils that have finer soil particles and more air spaces between them, the soil fumigant is able to thoroughly disperse and reach the target organism. With heavy or cloddy soils, fumigants injected into the soil cannot reach target organisms because air spaces between soil particles are blocked with water and tightly compacted. The large air spaces between clods in heavier soils serve as avenues for rapid dissipation of fumigants, thereby reducing periods of exposure of the soil fumigants to the soil and thus diminishing the efficaciousness on soil pathogens.

Another difficulty is that if the aforementioned soil fumigants are mixed in water, the mixture will often corrode the pipe or tubing carrying the fumigants to the soil, thus resulting in damage to the pipes.

Finally, traditional methods of soil fumigation may expose workers to soil fumigants. One of the concerns associated with the process of soil fumigation is worker exposure to soil biocides that may occur through contact or inhalation. For workers engaged in working with soil fumigants such as methyl bromide, chloropicrin, 1-3 dichloropropene, dimethyl disulphide, propargyl bromide, and methylisothiocyanate, and their mixtures, inhalation is the typical route of exposure.

One of the objects of the present invention is to address the aforementioned drawbacks associated with the prior art methods of soil fumigation.

SUMMARY OF THE INVENTION

One object of the present invention is to provide emulsified soil fumigants for use in drip irrigation systems that work just as effectively in both heavier soils and lighter, sandier soils so as to provide enhanced efficacy of soil biocides in controlling soil pathogens.

Another object of the invention is to provide a soil biocide formulation for use in drip irrigation systems that minimizes corrosion of pipes or tubing carrying the soil biocide formulation to the soil.

Yet another object of the present invention is to provide a soil biocide formulation that can be applied in such a way that minimizes workers' exposure to the soil fumigant.

In accordance with the present invention, a soil biocide formulation is provided for aqueous delivery with the formulation being comprised of an effective amount of a fumigant, for example, about 50 to 99% by weight of a the fumigant and about 50 to 1% by weight of an emulsifier comprised of non-ionic and anionic surfactants. Any fumigant, i.e., a chemical which exhibits biocidal properties and acts in the gaseous phase under normal conditions can be used with this invention, in addition to those specifically listed, and the preferred fumigants are selected from the group consisting of methyl bromide, chloropicrin, 1-3 dichloropropene, dimethyl disulphide, propargyl bromide, methylisothiocyanate, and their mixtures.

One advantage of the present invention is to provide emulsified soil fumigants for use in drip irrigation systems that work just as effectively in heavier soils and lighter, sandier soils so as to provide enhanced efficacy of soil fumigants in controlling soil pest organisms.

Another advantage of the invention is to provide a soil biocide formulation for use in drip irrigation systems that minimizes corrosion of the pipes or tubing carrying the soil biocide formulation to the soil, thus resulting in minimal damage to the pipes.

Yet another advantage of the present invention is that a soil biocide formulation in accordance with the present invention causes minimal exposure to workers involved in soil fumigation.

IN THE DRAWINGS

The aforementioned and other advantages and features of the present invention will become better understood upon reviewing the following detailed description of the invention taken in conjunction with the following drawings, where like numerals represent like elements, in which:

FIG. 3 is a graphical illustration of the properties displayed by the soil biocide chloropicrin when used in combination with PVC pipes such as black seamless latex, FEP Teflon, Nalgene 86-Tissue Culture Grade, Manosilt, Tygon, and Nalgene 180 premium PVC;

FIG. 4 is a table illustrating the effect of surfactant percentage in soil biocide formulation on the mortality of nematodes;

FIG. 5a shows the mortality rate of pigweed, amaranthus retroflexus, when treated with chloropicrin;

FIG. 5b is a bar graph illustrating the relationship between mortality rate of pigweed and concentrations of chloropicrin and emulsifier in the formulation;

FIG. 6a shows the mortality rate of white seed clover when treated with chloropicrin;

FIG. 7a shows the mortality rate of wild mustard when treated with chloropicrin;

FIG. 8a shows the mortality rate of yellow nut grass when treated with chloropicrin;

FIG. 9a shows the mortality rate of yellow sweet clover when treated with chloropicrin;

FIG. 10a shows the mortality rate of barnyard grass when treated with chloropicrin;

FIG. 10b is a bar graph illustrating the relationship between mortality rate of barnyard grass and concentrations of chloropicrin and emulsifier in the formulation;

FIG. 11a shows the mortality rate of bindweed when treated with chloropicrin.

DETAILED DESCRIPTION OF THE INVENTION

Figure 1:
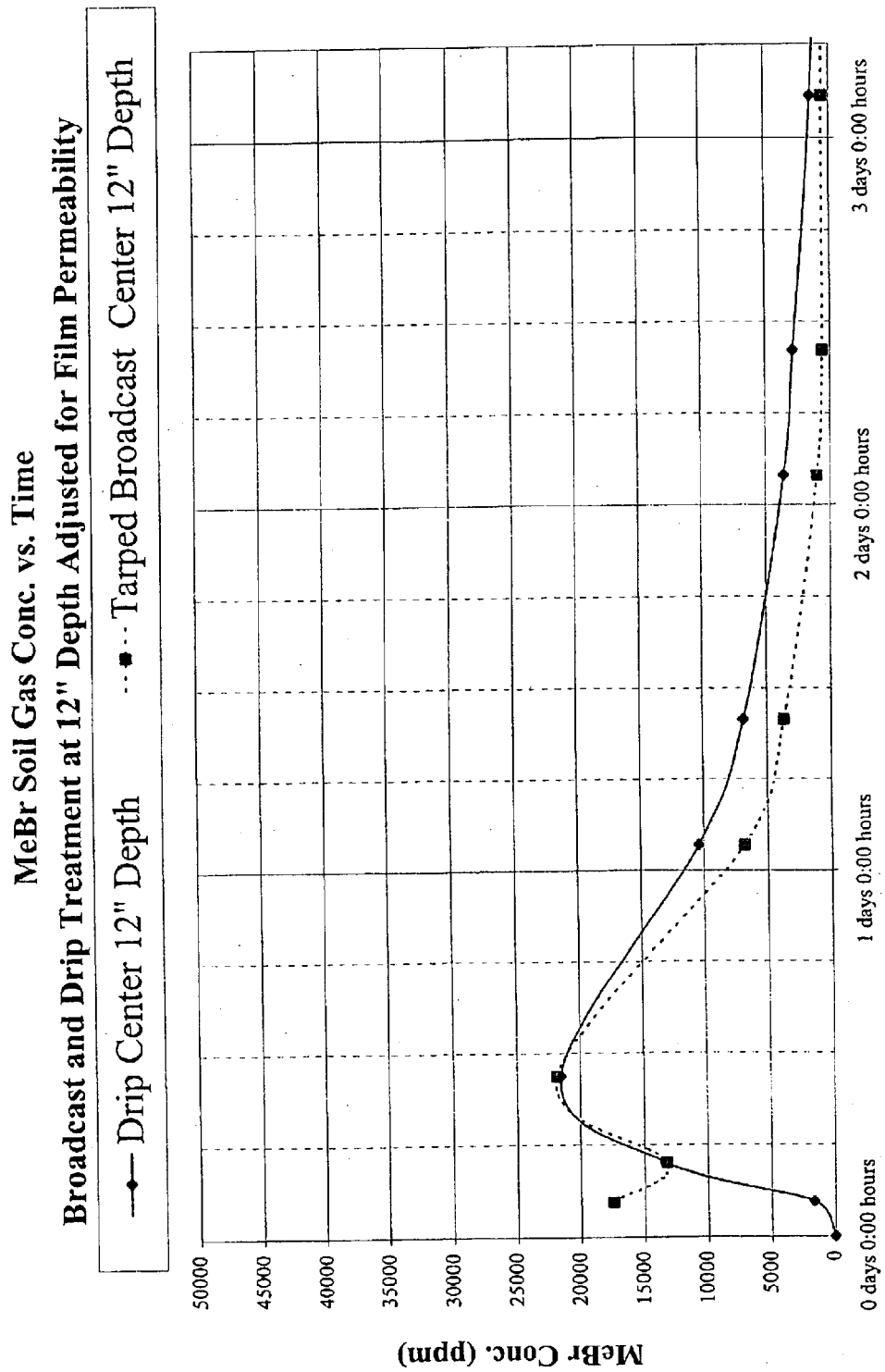
FIG. 1 is a graphical illustration of a comparison of soil gas concentrations of methyl bromide under polyethylene from a drip application versus a standard injection application.
Figure 2A:
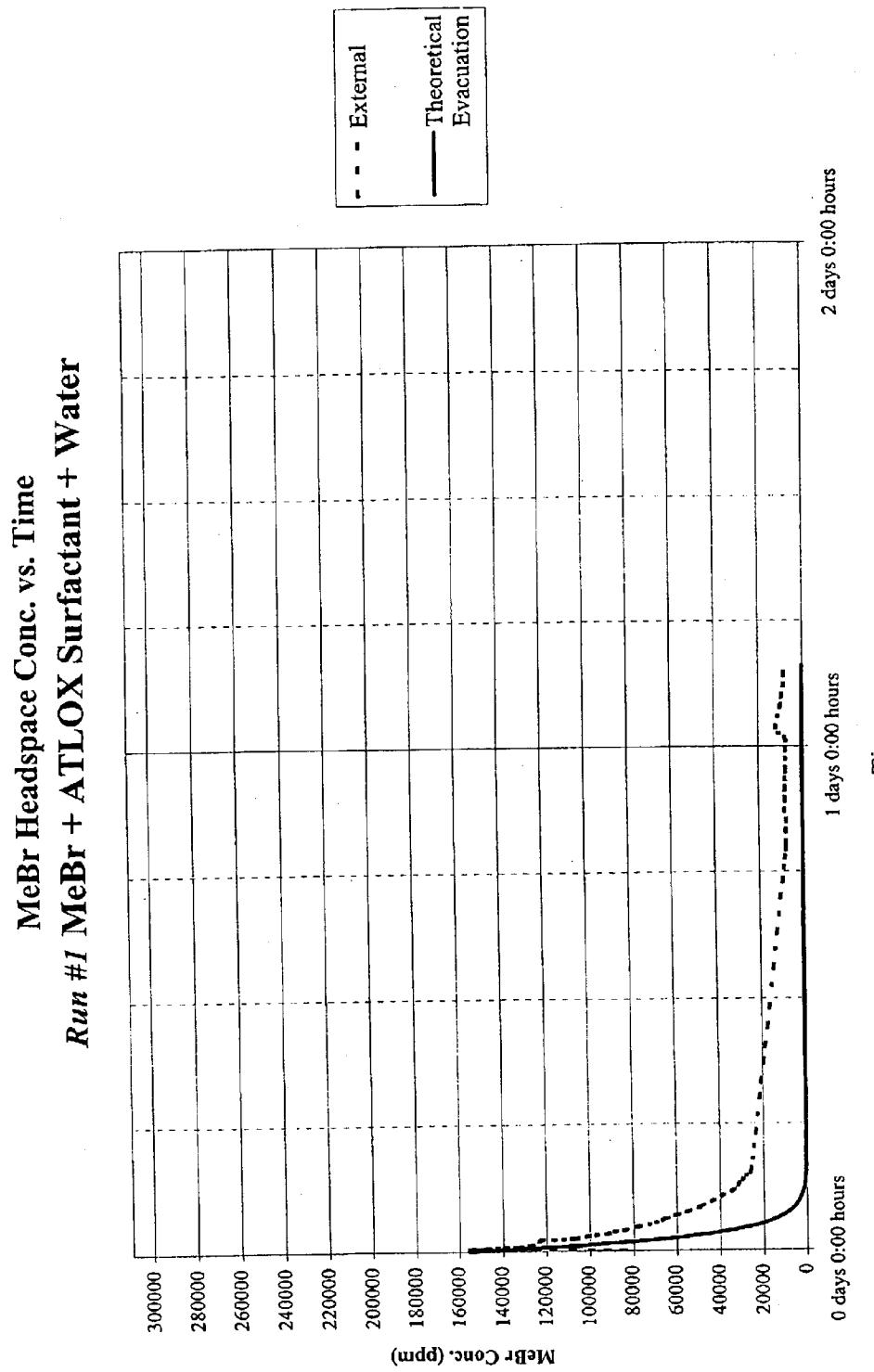
FIG. 2a is a graphical illustration of the volatilization rate of the biocide methyl bromide when used with surfactant and water and as observed in Run 1.
Figure 2B:
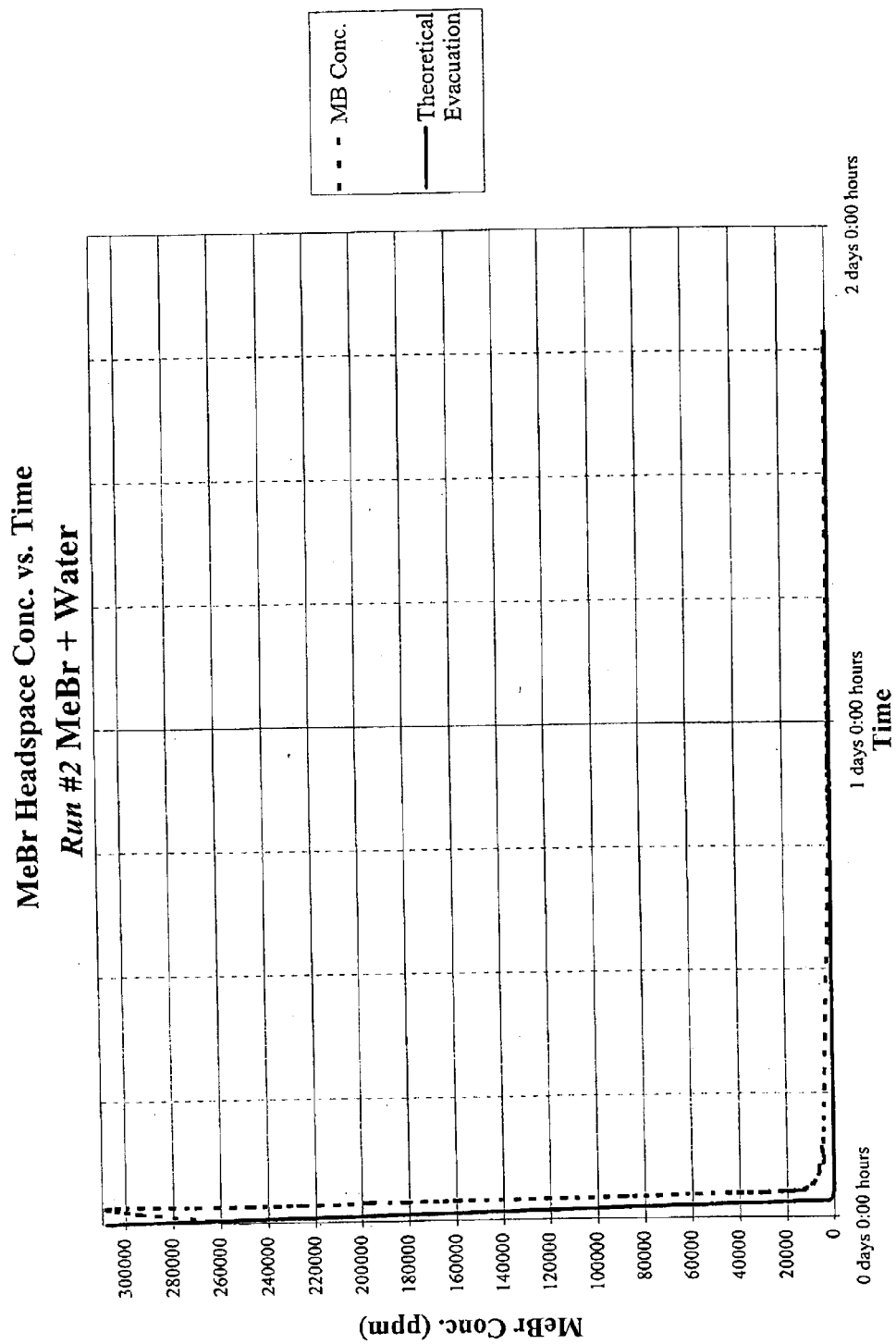
FIG. 2b is a graphical illustration of the volatilization rate of the biocide methyl bromide when used with water and as observed in Run 2.
Figure 2C:
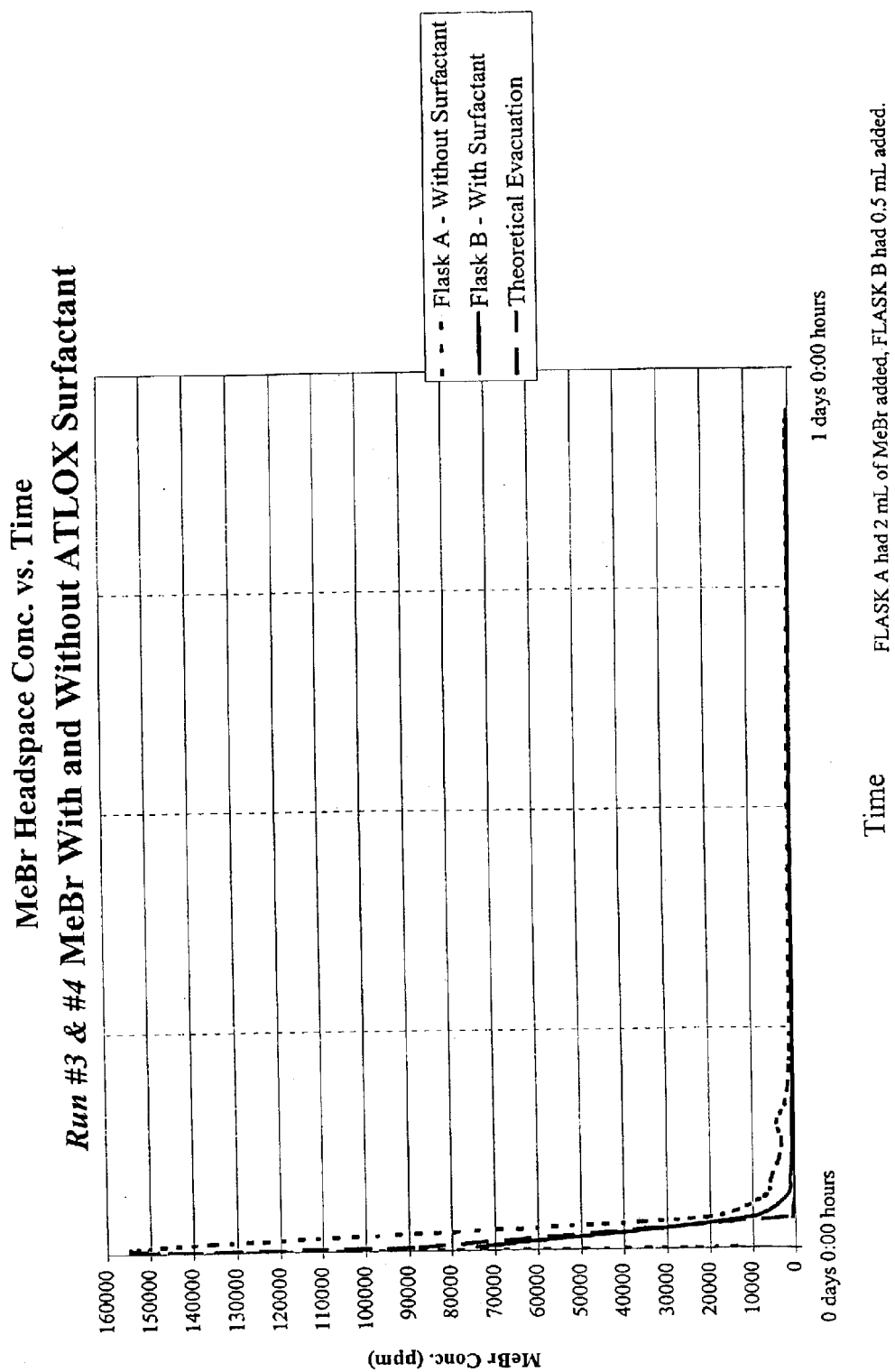
FIG. 2c is a graphical illustration of the volatilization rate of the biocide methyl bromide when used with and without the surfactant and as observed in Runs 3 and 4.

FIG. 1 is a graphical illustration of a comparison of the volatilization rate of methyl bromide under polyethylene from a drip application versus standard injection application. FIG. 1 illustrates that methyl bromide can be effectively applied in a drip irrigation system with water as a carrier, with concentrations equivalent to those from a standard injection system. As will be shown in FIGS. 2a–c are methyl bromide displays reduced partial pressure when present in a water matrix. Thus, application of methyl bromide and the other listed fumigants through drip systems provides a means of applying the fumagant in such a manner that may reduce emissions because of the reduced methyl bromide partial pressure when in a water matrix.

In accordance with the present invention, the fumigant methyl bromide has an application rate of 50–400 lbs. per acre, and preferably within the range of 150–400 lbs. per acre. The soil fumigant chloropicrin has an application rate of 50–300 obs per acre, and preferably 100–300 lbs. per acre. In accordance with the present invention, the soil fumigant 1,3 dichloropropene (Telone) has an application rate of 5–56 gal. per acre, and preferably 13–56 gal per acre. The soil fumigant dimethyl disulphide, has an application rate of 50 to 600 lbs. per acre, and preferably 100 to 500 lbs. per acre, and the soil fumigant propargyl bromide has an application rate of 50 to 400 lbs. per acre, and preferably 100 to 350 lbs. per acre. The soil biocide methylisothiocyanate has an application rate of 7 to 100 lbs. per acre.

FIGS. 2a–c are a graphical illustrations of the volatilization rate of the fumigant methyl bromide with and without the presence in a surfactant.

In accordance with one embodiment of the present invention, tests were conducted to determine if methyl bromide volatilizes at a different rate when it is in water solution as compared to a standard (theoretical) evacuation rate. In the present invention, samples of methyl bromide were obtained at the filling plant using 150 cc fumigant sample cylinders and the obtained samples were put in the laboratory freezer. After the samples were chilled, further samples were removed from the sample cylinders using chilled syringes and the samples were then injected into chilled flasks, already half filled with cold water. The injections were made under the surface of the water, while the sample cylinders were still in the freezer. Thereafter, flasks were immediately placed under the evacuation hood for collecting the samples obtained. Four runs were conducted using each of the following mixtures:

| | |
|---|---|
| Run 1 - MeBr/(5%) ATLOX surfactant/water | Flask 11 |
| Run 2 - MeBr/water | Flask 10 |
| Run 3 - MeBr/water | Flask 10 |
| Run 4 - MeBr/(5%) ATLOX surfactant/water | Flask 11 |

Air sampling pumps were used to maintain constant airflow through the flasks (~20 ml/min. for Runs 1 & 2, and 80 ml/min. for Runs 3 & 4). The headspace was sampled periodically with syringes as follows:

1. Run 1—56 Samples, 85 hours: 33 min.
2. Run 2—51 Samples, 19 hours: 7 min.
3. Run 3—16 Samples, 22 hours: 51 min.
4. Run 4—16 Samples, 22 hours: 51 min.

Runs 1 and 2 were carried out consecutively; Runs 3 and 4 were carried out simultaneously. All the pumps used for testing purposes had an identical flow rate.

The results of this test are depicted in the graphs in FIGS. 2a–c.

The curve of FIG. 2a illustrates the results of Run 1. The graph illustrates that degree of off-gassing of methyl bromide with surfactant and water is slower as compared to the standard rate of evacuation of methyl bromide. It also indicates that water plus 5% ATLOX surfactant increases the methyl bromide holding capacity of water even more. This further decreases the volatilization rate of methyl bromide.

FIG. 2b illustrates the results of Run 2. The figure illustrates that degree of off-gassing of methyl bromide with water is slower as compared to the theoretical or standard rate of evacuation of methyl bromide. The graph shows that mixing methyl bromide with water slows down its volatilization into the air above it. According to the present invention, the degree of off gassing of methyl bromide in a methyl bromide and water mixture is lower as compared to the degree of off-gassing of methyl bromide in a methyl bromide formulation without water. This shows that methyl bromide does not immediately-off-gas from water solutions because mixing methyl bromide with water slows down its volatilization into the air above it. This is a distinct advantage in soil fumigation applications because it ensures that methyl bromide remains in the soil for a longer time and is more efficacious in killing the target pest organisms. In comparison to the theoretical evacuation curve illustrating the volatilization rate, the slope of the curves from the data indicates that mixing methyl bromide with water slows down its volatilization into the air above it. Thus, application of methyl bromide and the other listed fumigants through drip systems provides another means of applying the material that may reduce emissions possibly because of the reduced methyl bromide partial pressure when in a water matrix.

FIG. 2c is a graphical illustration of the results of Runs 3 and 4 showing the volatilization rate of the soil biocide methyl bromide when used with the surfactant versus methyl bromide used without the surfactant.

In accordance with the present invention, the soil fumigant methyl bromide is mixed with an emulsifier/emulsifying agent to make the fumigant soluble in an aqueous media. The mixing of emulsifying agent with soil fumigants such as methyl bromide, chloropicrin, 1-3 dichloropropene, dimethyl disulphide, propargyl bromide, and methylisothiocyanate, which are immiscible compounds, makes their mixtures miscible in water. The emulsifying agent preferably has a water-attracting, hydrophilic component and a component with an affinity for the hydrophobic biocide, thus permitting the biocide to be mixed uniformly in irrigation water. The concentration of emulsifying agent in the soil biocide formulation is such that it surrounds molecules of the biocide creating an "oil in water emulsion." When fumigants such as methyl bromide, chloropicrin, 1-3 dichloropropene, dimethyl disulphide, propargyl bromide, and methylisothiocyanate, or their mixtures are emulsified, these chemical compounds cease to act as fumigants. Rather, the molecules of the emulsified biocide formulation move with the water through soil pores to the target pest organisms, instead of moving through air in soil. Moving with the water helps to more uniformly disperse and apply the biocide formulation through soil. The emulsified fumigants tend to remain in soil for longer periods and to maintain closer contact with target pest, thus providing a higher degree of control or suppression of soil pests than typically associated with the fumigant when applied through conventional soil fumigation methods.

Emulsifiers can be easily mixed with the fumigant as a pre-mix, in a tank in the field immediately prior to application, or simultaneously applied with the soil fumigant at the point of injection. The devices that are used for mixing include: static mixers, centrifugal pumps, numerous 90 degree bends in injection lines, etc. The emulsification of fumigants in water and subsequent application through a drip or trickle irrigation system provides for a higher degree and a broader spectrum of control or suppression of soil pests by using a lower concentration of soil biocides over a longer period of time as compared to traditional methods using fumigating apparatus drawn by a towing vehicle.

In accordance with a first embodiment of the present invention, the soil biocide formulation has a fumigant in the range of 50 to 99% and emulsifier in the range of 50 to 1%. This formulation can be applied for a duration long enough to deliver an effective amount of fumigant to the soil. Typically, the formulation can be applied at prescribed rates of up to 12 hours and more usually between 6 and 10 hours at an injection point along the drip irrigation system main, sub-main, or lateral water line.

In accordance with the present invention, a soil biocide formulation for aqueous delivery comprises about 50 to 99% by weight of the formulation of a fumigant, preferably selected from the group consisting of methyl bromide, chloropicrin, 1-3 dichloropropene, dimethyl disulphide, propargyl bromide, and methylisothiocyanate; and about 50 to 1% emulsifier. The emulsifier in accordance with the present invention comprises of one or more surfactants selected from the group consisting of non-ionic and anionic surfactants.

In a preferred embodiment, the biocide formulation for aqueous delivery comprises a more preferred range of about 80 to 95% by weight of a fumigant, preferably selected from the group consisting of methyl bromide, chloropicrin, 1-3 dichloropropene, dimethyl disulphide, propargyl bromide, and methylisothiocyanate and about 20 to 5% by weight of an emulsifier. In a further embodiment, the emulsifier component of the biocide formulation comprises anionic surfactant, in a range of 50 to 40% of the total weight of the surfactant, and a non-ionic surfactant in a range of 50 to 60% of the total weight of the surfactant. The soil biocide formulation may further comprise one or more solvents selected from the group consisting of ethoxylated castor oil and isopropyl alcohol.

FIG. 3 is an illustration of the properties displayed by the soil fumigant chloropicrin when used in combination with PVC pipes such as black seamless latex, FEP teflon, nalgene 86-tissue culture grade, manosilt, tygon, and nalgene 180 premium PVC.

High concentrations of soil biocides such as chloropicrin, 1,3-dichloropropene, and methylisothiocyanate, in particular, react with PVC irrigation pipes in which they flow, causing the main, sub-main, and lateral lines to weaken and rupture through a melting reaction. However, in accordance with the present invention, the use of an emulsifying agent permits the application of soil fumigants to crop soils while simultaneously minimizing the potential for damage to commonly used PVC drip or trickle irrigation systems. The table in FIG. 4 illustrates that none of the commonly used plastic pipes and tubing display any apparent reaction immediately after exposing the pipes and tubing to the soil biocide formulation comprising chloropicrin with a surfactant in an aqueous medium. The emulsifying agent preferably comprised of anionic and non-ionic surfactants has a tendency to surround the biocide particles. The emulsifier-coated biocide particles are then carried with water without adhering to or reacting with the inner walls of the irrigation system. Use of the emulsifier provides for enhanced dispersion of the biocide formulation in water and thus minimizing potentially high concentrations of soil biocides that are damaging to PVC.

In accordance with the present invention, after 15 hours of exposure, only some tubes like Tygon and Nalgene display some reaction and other pipes do not display any reaction whatsoever. This indicates that the soil biocide formulation prepared in accordance with the present invention does not have a propensity to damage the pipes used for carrying the soil biocide formulations in irrigation systems.

In accordance with the present invention, the application of soil fumigants in drip or trickle irrigation systems made possible by the use of the emulsifier reduces exposure of farm workers to fumes emanating from treated ground when compared to traditional methods using fumigating apparatus drawn by a towing vehicle. The drip application system is a closed system, which actually requires less handling of fumigants than the standard injection system. Also, the use of this system ensures that there is no need for workers to enter a field under treatment. Therefore, the only potential worker exposure is to the person monitoring the drip irrigation system. Further, the application of fumigants through drip systems provides another means of applying the material that may reduce emissions because of the reduced methyl bromide partial pressure when in a water matrix. As measured by field monitoring, exposure levels for drip-applied soil fumigants is significantly less as compared to tractor-drawn application equipment. The non-corrosive nature of the emulsified fumigants ensures that the PVC pipes carrying the soil biocide formulation do not corrode, leak, and subsequently expose workers to the soil biocide directly.

FIG. 4 is a table illustrating the effect of surfactant percentage in soil biocide formulation on the mortality of nematodes.

In the case of the present invention, tests were conducted by using PVC soil columns fabricated with uniform dimensions. Soil was mixed thoroughly so that the nematodes would be uniformly distributed among all of the soil tubes. Equal weights of soil in the soil columns to be treated were placed so that the headspace volume in each of the tubes was uniform. The headspace was approximately the top 3.5" depth of the column. Drip application tubes were placed into the soil 2 inches from the soil surface and the top of the tubes were covered with fumigation film. The soil settled after application resulting in an increase in the depth of headspace by approximately 3 inches. Tubes were covered on the top with a piece of polyethylene film to retain chloropicrin vapors in the headspace of the tube. Gas samples were collected from the headspace of each soil column at selected sampling intervals and then analyzed. Since chloropicrin concentrations in the headspace for many of the treatments were below the detection limit at 'peak emission', sampling was terminated after initial intervals.

As shown in FIG. 4, Chloropicrin appeared to have a significant effect on the mortality of citrus and dagger (xiphinema) nematode. There was no significant difference between the treatments for the root knot (meloidogyne) and pin nematodes. Pin nematode counts were zero or low in all treatments, however, including the control.

Table 1 illustrates the efficacy of chloropicrin when used with root knot nematode.

Anova: Single Factor at 462 ppm Chloropicrin

SUMMARY

| Groups | Count | Sum | Average | Variance |
|---|---|---|---|---|
| Control | 5 | 231 | 46.2 | 3881.7 |
| 0% Emulsifier | 5 | 540 | 108 | 17302.5 |
| 5% Emulsifier | 5 | 612 | 122.4 | 15675.3 |
| 50% Emulsifier | 5 | 657 | 131.4 | 7224.3 |

ANOVA

| Source Variation | SS | df | ms | F | P = value | F crit |
|---|---|---|---|---|---|---|
| Between Groups | 22150.8 | 3 | 7383.6 | 0.6699604 | 0.582765 | 3.238867 |
| Within Groups | 176335.2 | 16 | 11020.95 | | | |
| Total | 198486 | 19 | | | | |

Table 2 is an illustration of efficacy of chloropicrin on dagger (xiphinema) nematode at 462 ppm chloropicrin.

| Groups | Count | Sum | Average | Variance |
|---|---|---|---|---|
| Control | 5 | 27 | 5.4 | 28.8 |
| 0% Emulsifier | 5 | 0 | 0 | 0 |
| 5% Emulsifier | 5 | 0 | 0 | 0 |
| 50% Emulsifier | 5 | 0 | 0 | 0 |

ANOVA

| Source Variation | SS | df | ms | F | P = value | F crit |
|---|---|---|---|---|---|---|
| Between Groups | 109.35 | 3 | 36.45 | 5.0625 | 0.0118033 | 3.238867 |
| Within Groups | 115.2 | 16 | 7.2 | | | |
| Total | 224.55 | 19 | | | | |

Table 3 is an illustration of the efficacy of chloropicrin when used on citrus nematode at 462 ppm chloropicrin.

| Groups | Count | Sum | Average | Variance |
|---|---|---|---|---|
| Control | 5 | 3555 | 711 | 261594 |
| 0% Emulsifier | 5 | 1155 | 231 | 6246 |
| 5% Emulsifier | 5 | 1332 | 266 | 31722 |
| 50% Emulsifier | 5 | 1071 | 214 | 10326 |

ANOVA

| Source Variation | SS | df | ms | F | P = value | F crit |
|---|---|---|---|---|---|---|
| Between Groups | 848924.55 | 3 | 282974.85 | 3.652608 | | 3.238867 |
| Within Groups | 1239552 | 16 | 77472 | | | |
| Total | 2088476.6 | 19 | | | | |

Table 4 is an illustration of the efficacy of chloropicrin on citrus nematode minus low outlier at 462 ppm chloropicrin.

| Groups | Count | Sum | Average | Variance |
|---|---|---|---|---|
| Control | 4 | 3534 | 884 | 150417 |
| 0% Emulsifier | 4 | 1035 | 259 | 3194.25 |
| 5% Emulsifier | 4 | 1242 | 311 | 29331 |
| 50% Emulsifier | 4 | 1020 | 255 | 2670 |

ANOVA

| Source Variation | SS | df | ms | F | P = value | F crit |
|---|---|---|---|---|---|---|
| Between Groups | 1119426.2 | 3 | 373142.06 | 8.0413241 | | 3.4902996 |
| Within Groups | 556836.75 | 12 | 46403.063 | | | |
| Total | 1676262.9 | 15 | | | | |

Table 5 is an illustration of the efficacy of chloropicrin on citrus nematode minus low outlier at 462 ppm chlorpicrin.

| Groups | Count | Sum | Average | Variance |
|---|---|---|---|---|
| Control | 4 | 3534 | 883.5 | 150417 |
| 0% Emulsifier | 4 | 1035 | 258.75 | 3194.25 |
| 5% Emulsifier | 4 | 1242 | 310.5 | 29331 |
| 50% Emulsifier | 4 | 1020 | 255 | 2670 |

ANOVA

| Source Variation | SS | df | ms | F | P = value | F crit |
|---|---|---|---|---|---|---|
| Between Groups | 1119426.2 | 3 | 373142.06 | 8.0413241 | 0.0033314 | 5.952591 |
| Within Groups | 556836.75 | 12 | 46403.063 | | | |
| Total | 1676262.9 | 15 | | | | |

Table 6 is an illustration of the efficacy of chloropicrin on pin nematode at 462 ppm chloropicrin.

| Groups | Count | Sum | Average | Variance |
|---|---|---|---|---|
| Control | 5 | 111 | 22.2 | 1330.2 |
| 0% Emulsifier | 5 | 54 | 10.8 | 331.2 |
| 5% Emulsifier | 5 | 0 | 0 | 0 |
| 50% Emulsifier | 5 | 0 | 0 | 0 |

ANOVA

| Source Variation | SS | df | ms | F | P = value | F crit |
|---|---|---|---|---|---|---|
| Between Groups | 1686.15 | 3 | 562.05 | 1.353196 | | 3.238867 |
| Within Groups | 6645.6 | 16 | 415.35 | | | |
| Total | 8331.75 | 19 | | | | |

FIG. 5a is an illustration of the efficacy of chloropicrin, when used according to the method of the presently claimed invention in an aqueous medium on killing pigweed, *Amaranthus retroflexus*.

The tests to determine the efficacy of chloropicrin, when used with the surfactant of the presently claimed invention in an aqueous medium on killing pigweed, *Amaranthus retroflexus*, were performed in petrie dishes. Aliquots of mixtures of the respective treatments were applied to the petrie dishes of seeds and the seeds were left exposed for 24 hours. After the 24 hour exposure period, the seeds were rinsed with 5 ml water spray mist. The seeds were then moistened as needed for the duration of the experiment. Germination counts were made at approximately 8 and 12 days. Seeds were monitored for a longer time, but results remained the same after 12 days.

As shown in FIG. 5a, close to 100% mortality was observed at the end of 12 days for the pigweed, *Amaranthus retroflexus*. When this statistic was adjusted for control, roughly 65% mortality was observed.

FIG. 5b is a bar graph illustrating the relationship between mortality rate of pigweed and concentrations of chloropicrin and emulsifier in the formulation. The greatest mortality level was observed when the weed seeds were treated with the highest concentration of the chloropicrin biocide formulation of 1000 ppm, containing a 50% emulsifier, however, all rates were statistically equivalent.

Figure 6A:
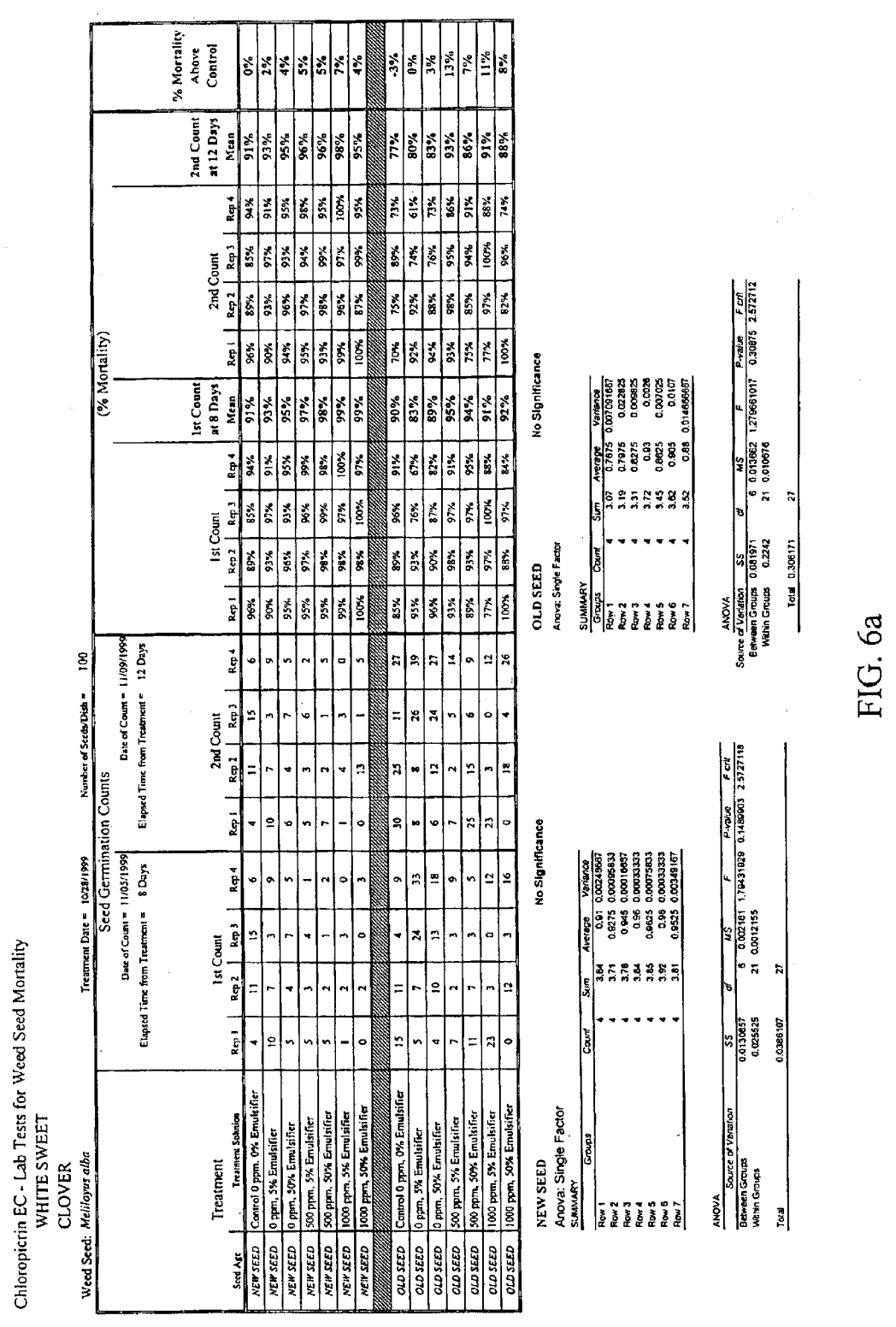

As shown in FIG. 6a, close to 95% mortality was observed at the end of 12 days for white sweet clover treated with the chloropicrin formulation in accordance with the present invention.

Figure 6B:
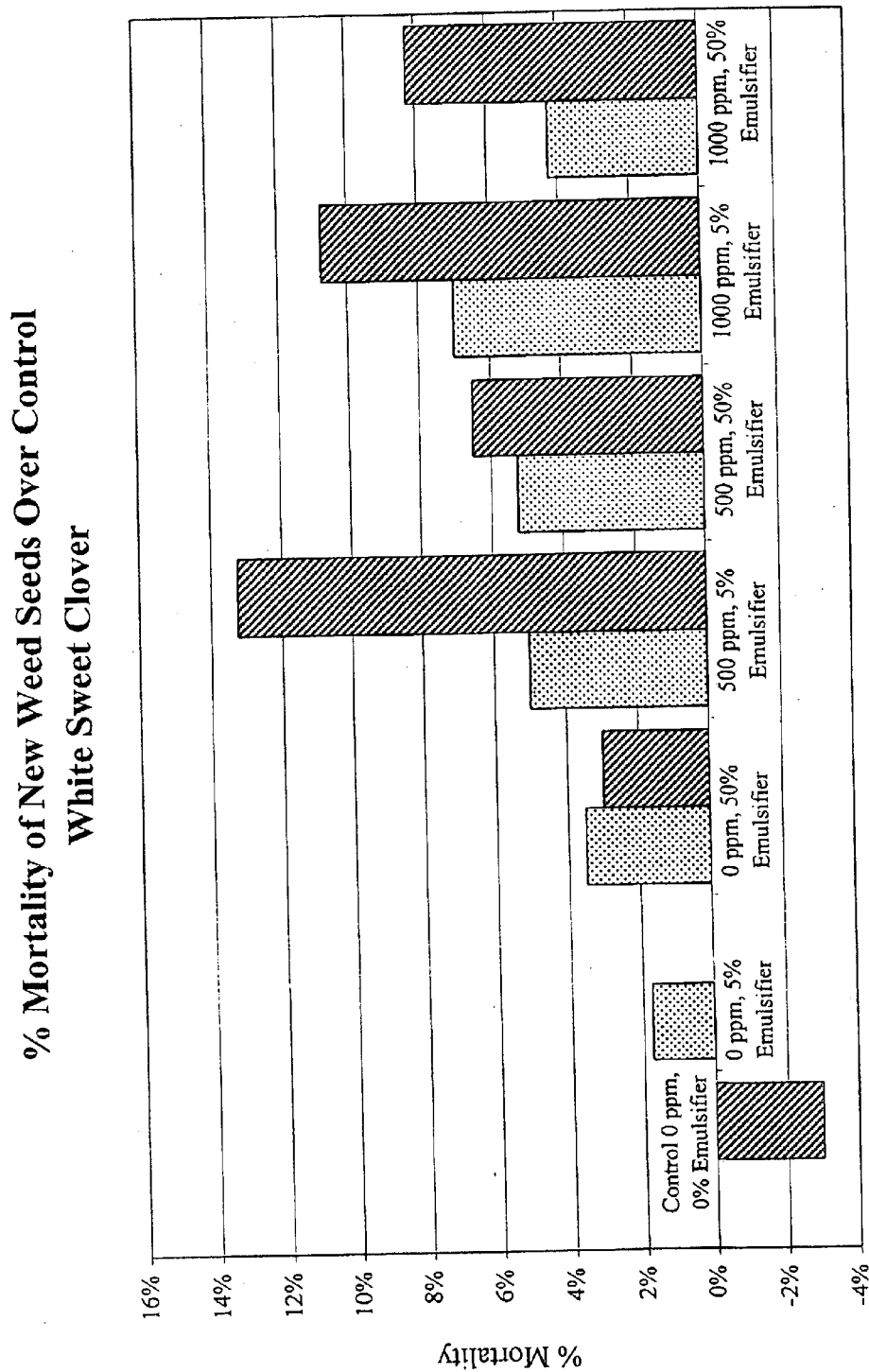
FIG. 6b is a bar graph illustrating the relationship between mortality rate of white seed clover and concentrations of chloropicrin and emulsifier in the formulation.

FIG. 6b is a bar graph illustrating the relationship between mortality rate of white sweet clover and concentrations of chloropicrin and emulsifier in the formulation. The greatest mortality level was observed when the weed seeds were treated with the chloropicrin biocide formulation at a 500 ppm application rate and 5% of the formulation being the emulsifier, however, all rates were statistically equivalent.

As shown in FIG. 7a, close to 75% mortality was observed at the end of 12 days for the wild mustard.

Figure 7B:
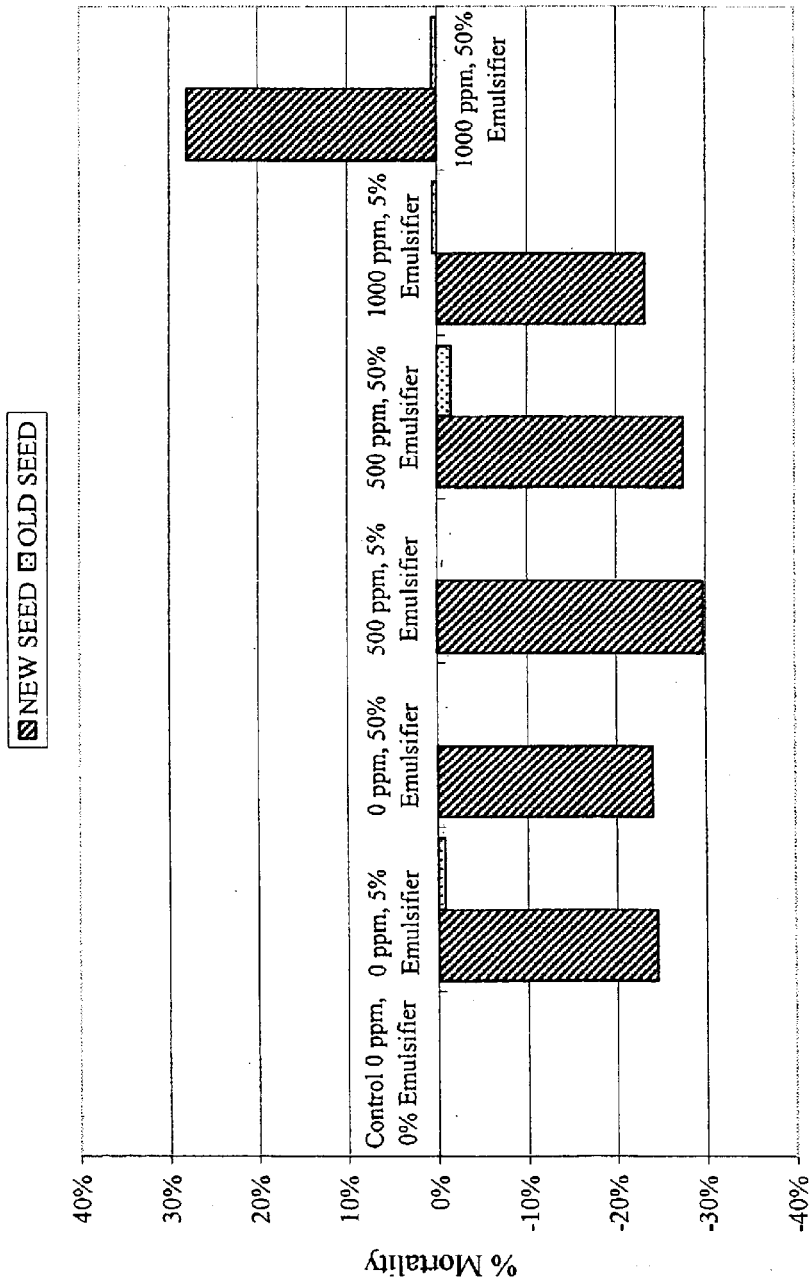
FIG. 7b is a bar graph illustrating the relationship between mortality rate of wild mustard and concentrations of chloropicrin and emulsifier in the formulation.

FIG. 7b is a bar graph illustrating the relationship between mortality rate of wild mustard and concentrations of chloropicrin and emulsifier in the formulation. The greatest mortality level was observed when the weed seeds were treated with the chloropicrin biocide formulation at a 500 ppm application rate, with 5% of the formulation being an emulsifier, however, all rates were statistically equivalent.

As shown in FIG. 8a, close to 100% mortality was observed at the end of 12 days for the yellow nut grass treated with the chloropicrin formulation in accordance with the present invention.

Figure 8B:
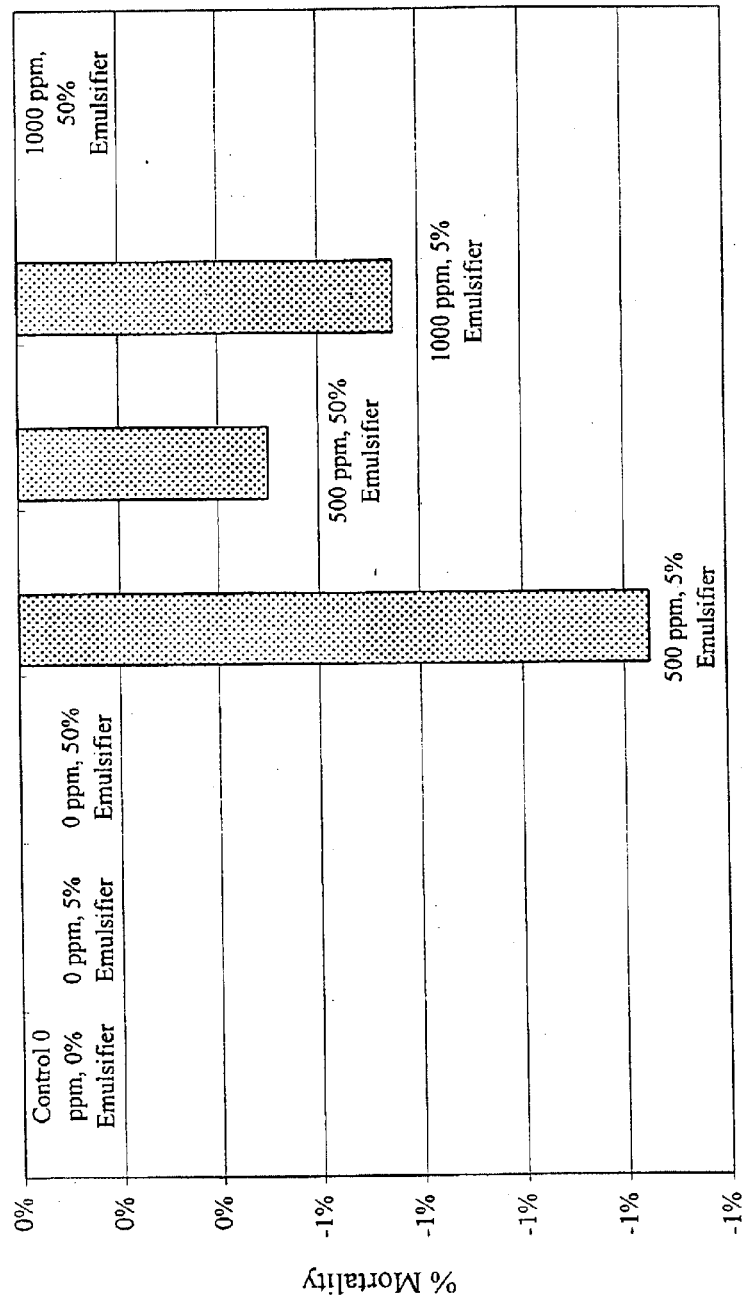
FIG. 8b is a bar graph illustrating the relationship between mortality rate of yellow nut grass and concentrations of chloropicrin and emulsifier in the formulation.

FIG. 8b is a bar graph illustrating the relationship between mortality rate of yellow nut grass and concentrations of chloropicrin and emulsifier in the formulation. The greatest mortality level was observed when the weed seeds were treated with the chloropicrin biocide formulation at a 500 ppm application rate with 5% of the formulation being emulsifier, however, all rates were statistically equivalent.

Figure 9A:
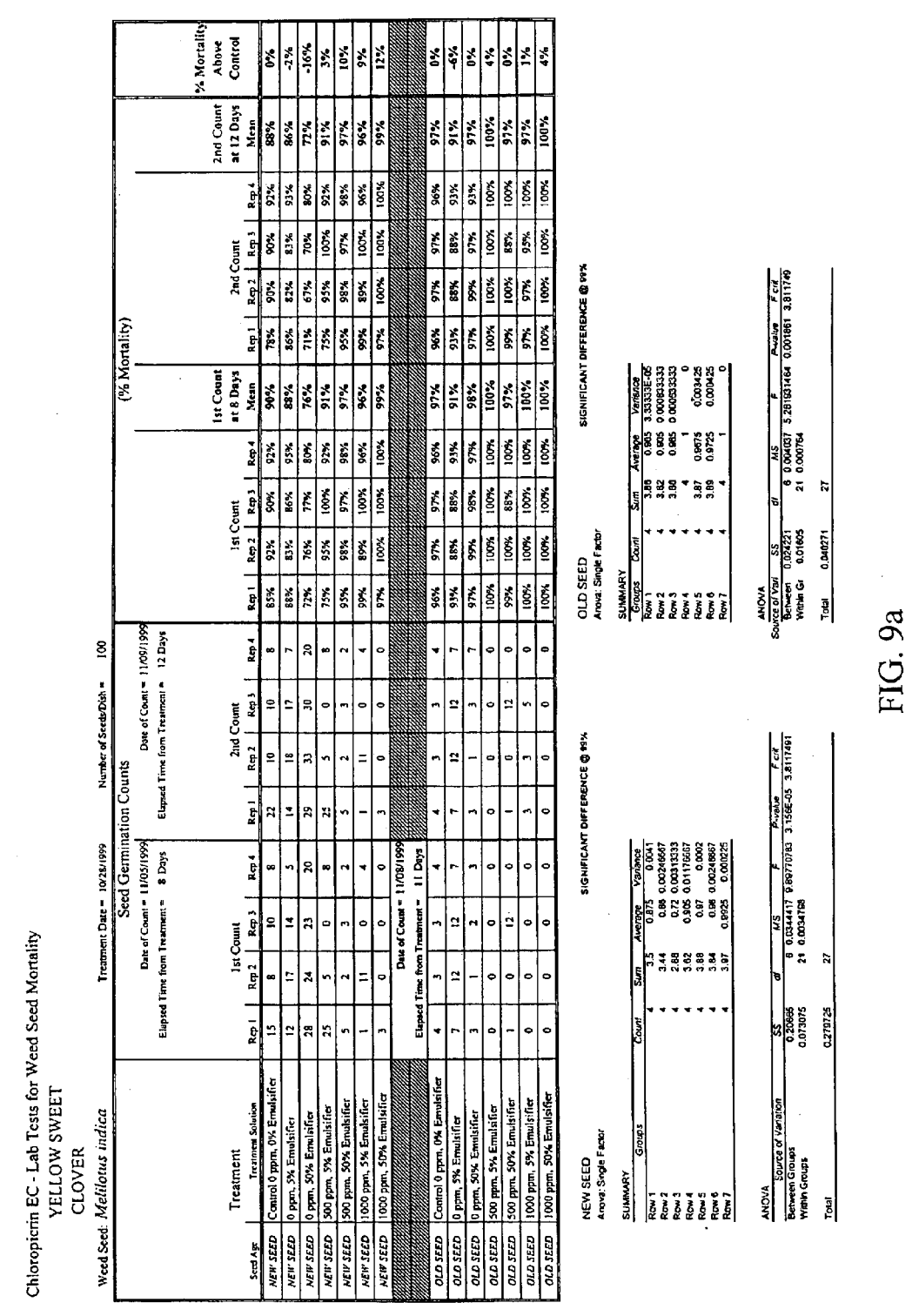

As shown in FIG. 9a, close to 95% mortality was observed at the end of 12 days for the white sweet clover treated with the chloropicrin formulation in accordance with the present invention.

Figure 9B:
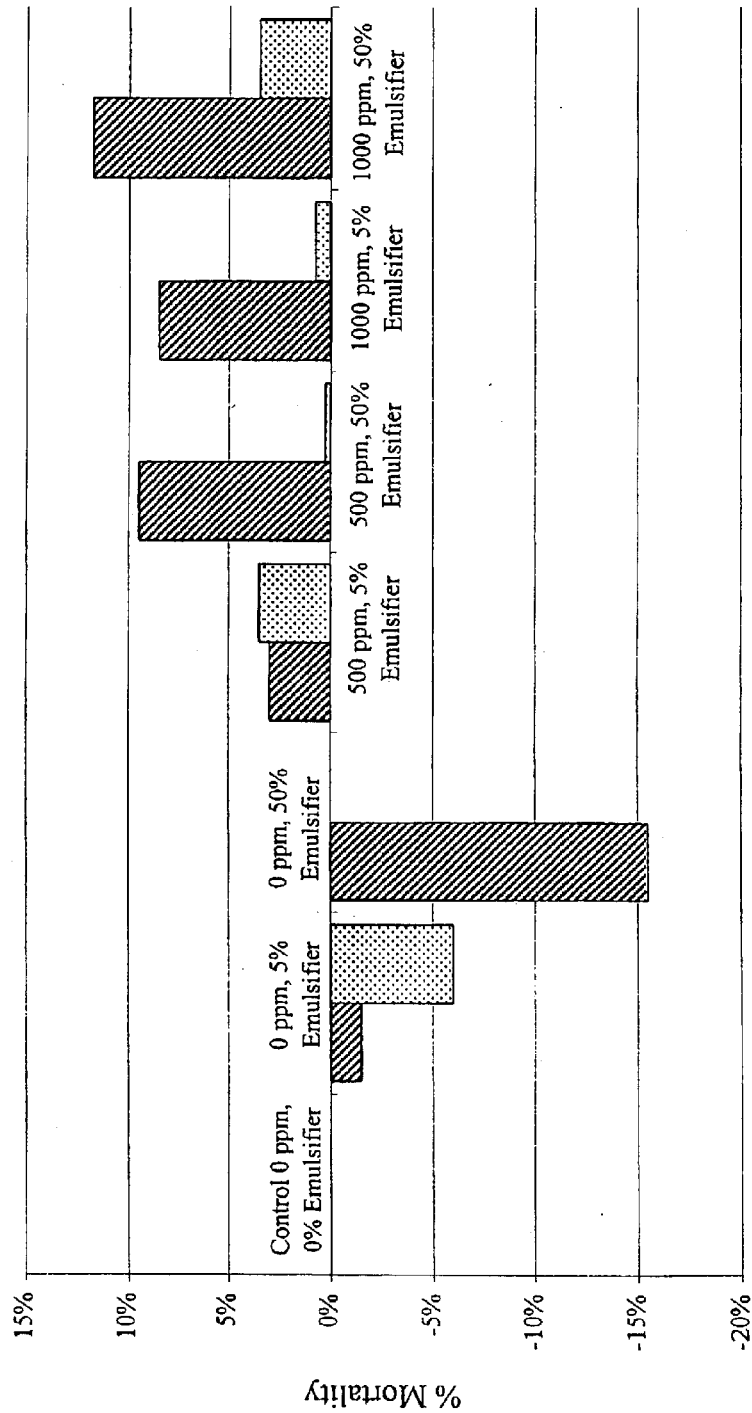
FIG. 9b is a bar graph illustrating the relationship between mortality rate of yellow sweet clover and concentrations of chloropicrin and emulsifier in the formulation.

FIG. 9b is a bar graph illustrating the relationship between mortality rate of yellow nut grass and concentrations of chloropicrin and emulsifier in the formulation. The greatest mortality level was observed when the weed seeds were treated with the chloropicrin biocide formulation at a 1000 ppm application rate with 50% of the formulation being emulsifier, however, all rates were statistically equivalent.

Figure 10A:
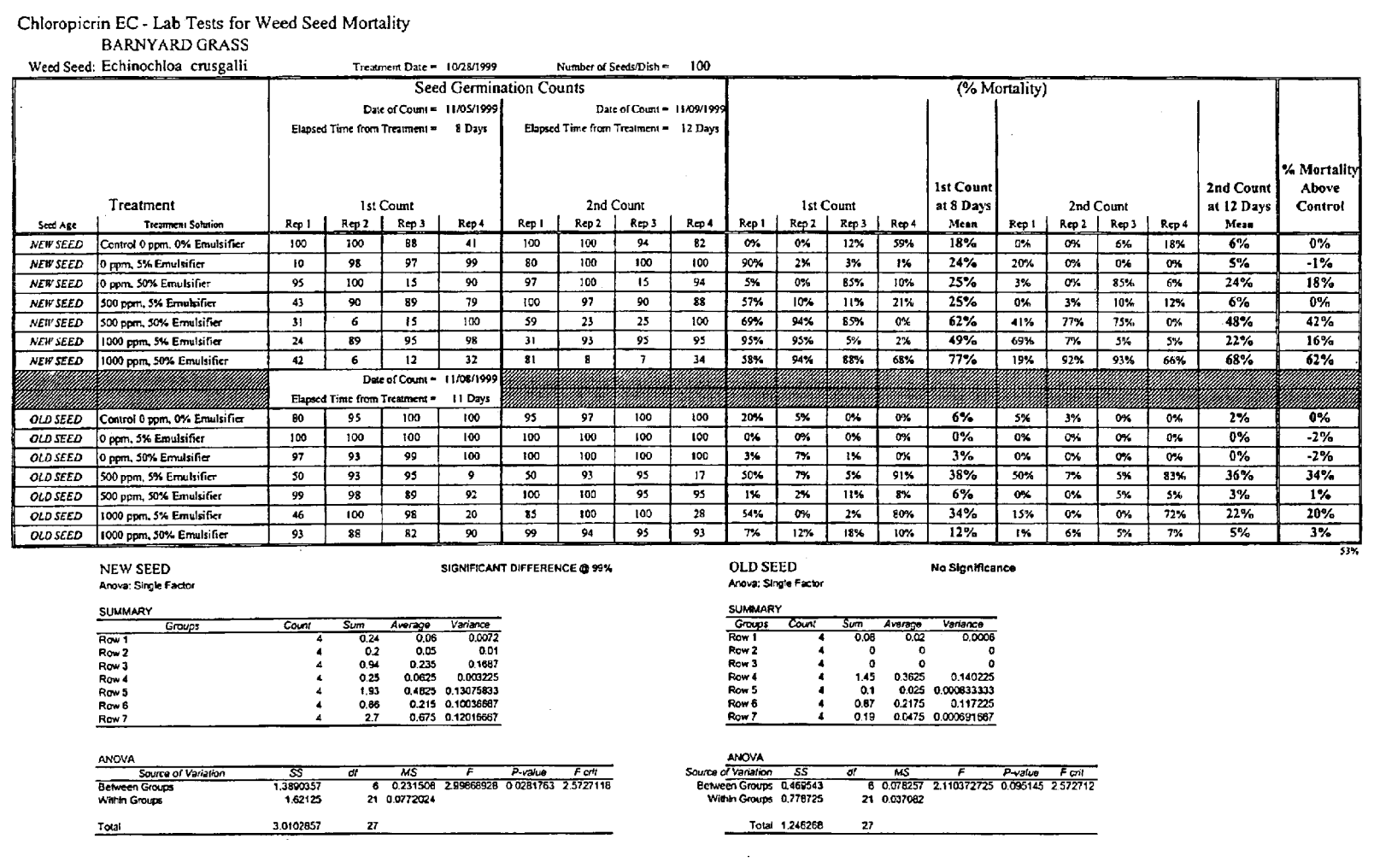

As shown in FIG. 10a, close to 68% mortality was observed at the end of 12 days for the barnyard grass treated with the chloropicrin formulation in accordance with the present invention.

FIG. 10b is a bar graph illustrating the relationship between mortality rate of yellow nut grass and concentrations of chloropicrin and emulsifier in the formulation. The greatest mortality level was observed when the weed seeds were treated with the chloropicrin biocide formulation at a 1000 ppm application rate with 50% of the formulation being emulsifier, however, all rates were statistically equivalent.

As shown in FIG. 11a, close to 90% mortality was observed at the end of 12 days for the bindweed treated with the chloropicrin formulation in accordance with the present invention.

Figure 11B:
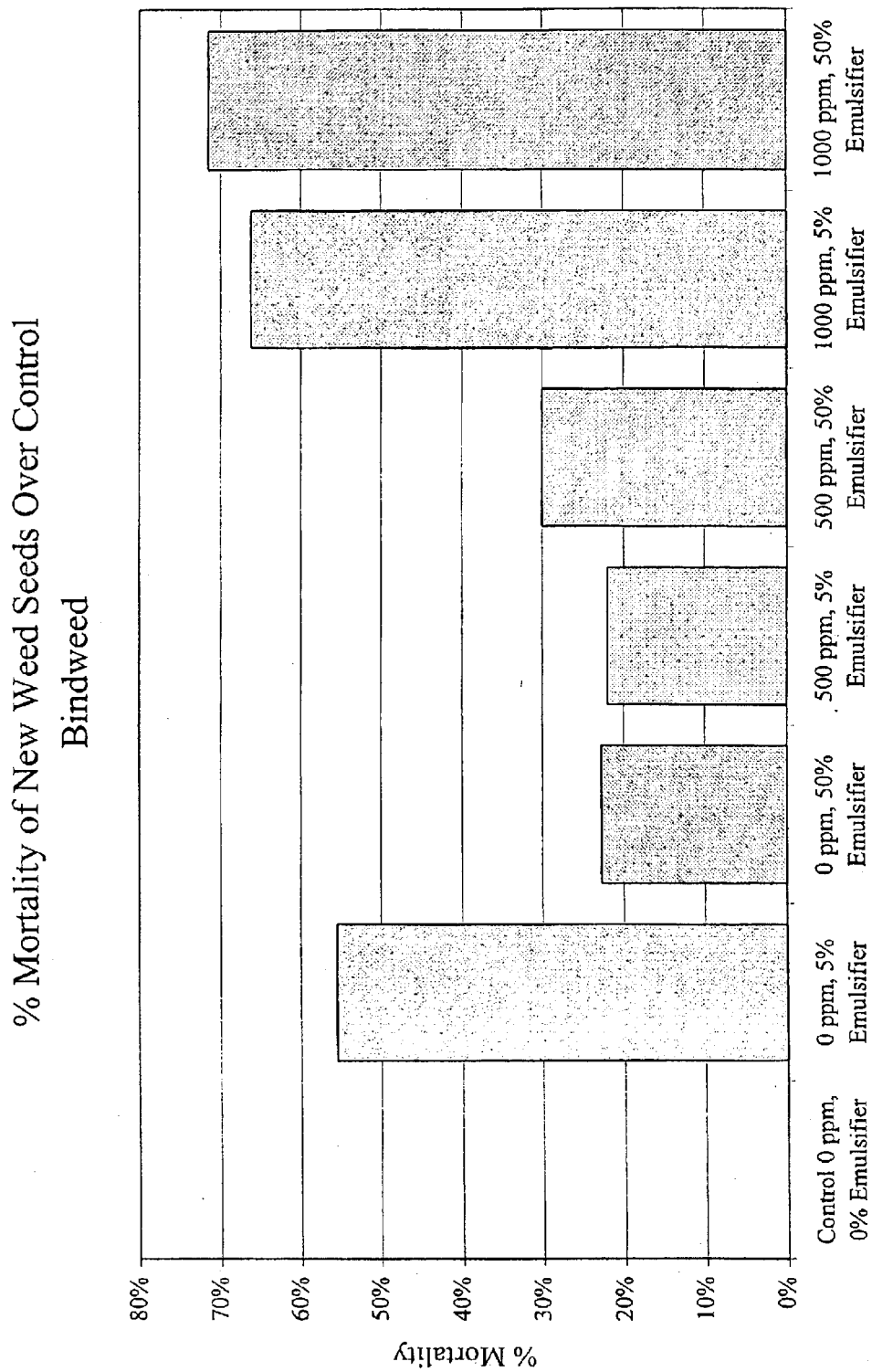
FIG. 11b is a bar graph illustrating the relationship between mortality rate of bindweed and concentrations of chloropicrin and emulsifier in the formulation.

FIG. 11b is a bar graph illustrating the relationship between mortality rate of yellow nut grass and concentrations of chloropicrin and emulsifier in the formulation. The greatest mortality level was observed when the weed seeds were treated with the chloropicrin biocide formulation at a 1000 ppm application rate with 50% of the formulation being emulsifier, however, all rates were statistically equivalent.

Whereas the present invention may be embodied in many forms, details of a preferred embodiment are shown in FIGS. 1 through 11b, with the understanding that the present disclosure is not intended to limit the invention to the embodiment illustrated. Other fumigants in addition to those specifically listed can be used in preparing the biocide formulation in accordance with the present invention, as can surfactants other than those specifically listed. While the invention has been particularly shown and described with reference to certain embodiments, it will be understood by those skilled in the art that various alterations and modifications in form and detail may be made therein. Accordingly, it is intended that the following claims cover all such alterations and modifications as fall within the true spirit and scope of the invention.

What is claimed is:

1. A method for applying a soil biocide formulation to soil comprising:

adding to an aqueous medium an effective amount of
a soil fumigant, and
a surfactant containing nonylphenol ethoxylate in an amount from approximately 50 to 90% by weight, castor oil ethocylate in an amount from approximately 10 to 40% by weight, isopropyl amine dodecyl benzene sulfornate in an amount from approximately 0.1 to 10% by weight, and isopropyl alcohol in an amount from approximately 0.1 to 30% by weight creating a resulting mixture; and,
applying the resulting mixture to the soil.

2. A method for applying a soil biocide as recited in claim 1 wherein the resulting mixture is applied to the soil in a drip irrigation system.

3. A method for applying a soil biocide as recited in claim 2 wherein said drip irrigation system comprises components made of plastic.

4. A method for applying a soil biocide formulation as recited in claim 1, wherein said soil fumigant selected from the group consisting of methyl bromide, chloropicrin, dimethyl disulphide, propargyl bromide, and methylisothiocyanate.

5. The method as recited in claim 4, wherein said soil fumigant comprises dimethyl disulphide having an application rate of approximately 50–600 lbs per acre.

6. The method as recited in claim 4, wherein said soil fumigant comprises propargyl bromide having an application rate of approximately 50–400 lbs per acre.

* * * * *